United States Patent
McLeod et al.

(10) Patent No.: US 9,424,398 B1
(45) Date of Patent: Aug. 23, 2016

(54) WORKFLOWS FOR DEFINING A SEQUENCE FOR AN ANALYTICAL INSTRUMENT

(75) Inventors: Fraser S. McLeod, Munich (DE); Peter Sauter, Munich (DE); Markus Roming, Herrsching (DE)

(73) Assignee: DIONEX CORPORATION, Sunnyvale, CA (US)

( * ) Notice: Subject to any disclaimer, the term of this patent is extended or adjusted under 35 U.S.C. 154(b) by 630 days.

(21) Appl. No.: 12/645,280

(22) Filed: Dec. 22, 2009

Related U.S. Application Data

(60) Provisional application No. 61/147,083, filed on Jan. 24, 2009, provisional application No. 61/152,643, filed on Feb. 13, 2009.

(51) Int. Cl.
  *G06Q 10/00* (2012.01)
  *G06F 19/00* (2011.01)

(52) U.S. Cl.
  CPC ......... *G06F 19/366* (2013.01); *G06F 19/3406* (2013.01)

(58) Field of Classification Search
  CPC .... G06Q 10/06; G06Q 10/063; G06Q 50/00; G01N 30/24; G06F 19/366; G06F 19/3406; G06F 19/3418
  USPC ........................ 705/1.1, 7.26, 7.23
  See application file for complete search history.

(56) References Cited

U.S. PATENT DOCUMENTS

| | | | |
|---|---|---|---|
| 7,475,050 B2 | 1/2009 | Larson | 706/47 |
| 7,555,672 B2 | 6/2009 | Berman et al. | 714/2 |
| 7,925,330 B2 * | 4/2011 | Kalafut et al. | 600/431 |
| 2003/0045000 A1 * | 3/2003 | Frank et al. | 436/180 |
| 2004/0078105 A1 * | 4/2004 | Moon et al. | 700/100 |
| 2004/0253147 A1 * | 12/2004 | Golushko | 422/71 |
| 2005/0165574 A1 * | 7/2005 | Arthursson et al. | 702/127 |
| 2006/0074735 A1 * | 4/2006 | Shukla et al. | 705/8 |
| 2007/0071650 A1 * | 3/2007 | Wang | 422/83 |
| 2007/0112804 A1 * | 5/2007 | DeSimas et al. | 707/100 |
| 2007/0236708 A1 * | 10/2007 | Jahn et al. | 358/1.6 |
| 2007/0295113 A1 * | 12/2007 | Londo et al. | 73/864.34 |
| 2009/0044185 A1 * | 2/2009 | Krivopaltsev | 717/173 |
| 2009/0138318 A1 * | 5/2009 | Hawkins et al. | 705/9 |
| 2009/0247417 A1 * | 10/2009 | Haas et al. | 506/8 |
| 2013/0218352 A1 * | 8/2013 | Iovanni et al. | 700/282 |

* cited by examiner

*Primary Examiner* — Johnna Loftis
(74) *Attorney, Agent, or Firm* — Douglas J. Crisman

(57) ABSTRACT

Methods, systems and GUIs for defining a sequence of analyzes for an analytical instrument using a workflow are described. A method includes receiving user inputs including workflow parameters for defining the sequence, and automatically defining the sequence for the analytical instrument based on the workflow parameters, including creating rules for the sequence. The rules are persistent for subsequent use of the sequence. The rules are defined by the user, e.g., an administrator, who creates or edits the workflow. The administrator can leave some choices available to operators who run the workflow, or can lock selections down.

35 Claims, 22 Drawing Sheets

In order to generate an eWorkflow the editor is split into three sections.
The sections should be completed in the following order:

eWorkflow General → Sequence General → Sequence Layout

WORKFLOWS FOR DEFINING A SEQUENCE FOR AN ANALYTICAL INSTRUMENT

RELATED APPLICATIONS

This application claims the benefit of U.S. Provisional Application No. 61/147,083, titled "Workflows for Defining a Sequence for an Analytical Instrument" filed Jan. 24, 2009 which application is incorporated by reference herein in its entirety.

This application is related to U.S. patent application Ser. No. 12/359,253, titled "Baseline Alternatives For Unresolved Peaks," filed Jan. 23, 2009, which application is incorporated by reference herein in its entirety.

This application is related to of U.S. Provisional Application No. 61/152,643, titled "Representing a Plot with a Mini-Plot" filed Feb. 13, 2009 which application is incorporated by reference herein in its entirety.

This application is related to of U.S. application Ser. No. 12/626,394, titled "Representing a Plot with a Mini-Plot" filed Nov. 25, 2009 which application is incorporated by reference herein in its entirety.

TECHNICAL FIELD

The disclosed embodiments relate generally to workflow management and in particular to workflow management for defining a sequence for an analytical measurement instrument.

BACKGROUND

Typically, sequences for analytical measurement instruments (e.g., chromatography instruments) are manually created in a table by appending injections and then manually setting all parameters like type, injection volume, instrument method, and processing method etc. of the injections. Usually the sequence is also associated with a certain instrument. Creating a sequence manually can take a lot of time and is error prone because many parameters have to be filled in again and again. A common way to overcome this limitation is to create sequence templates, copy them to a new location and filling in the missing parameters. However, even then there may be no built-in control of where the sequence is copied. There may also be no built-in control over preventing users from modifying the sequence in a way which is incompatible with the template requirements. It is still possible to enter wrong parameters or to use the wrong instrument.

SUMMARY

Some embodiments provide methods, systems, and graphical user interfaces (GUIs) for receiving user inputs including workflow parameters for defining a sequence of analyses for an analytical laboratory instrument, and automatically defining the sequence for the analytical laboratory instrument based on the workflow parameters. In some embodiments, defining the sequence includes creating rules for the sequence, wherein the rules are persistent for subsequent use of the sequence.

A skilled operator such as an administrator can define the sequence of analyses including locking certain selections. Then a less skilled operator can run generate sequences according to the rules. As such, some embodiments further include, restricting use of the sequence to the analytical laboratory instrument for which it is defined.

In some embodiments, the workflow parameters include one or more of: a workflow type, an instrument for which the sequence is to be defined, one or more methods that make up a sequence, and one or more associated files.

Some embodiments further include, receiving user inputs including changes to the workflow parameters for defining the sequence, and automatically updating the sequence based on the changes to the workflow parameters and in accordance with the rules for the sequence.

Some embodiments further include, receiving user inputs including changes to a lifecycle state of the workflow. The lifecycle state is one of: workflow in development, workflow ready for use, workflow approved for use, and workflow retired. Then some embodiment include automatically updating the lifecycle state of the workflow based on the changes, and permitting use of the sequence based on the lifecycle state of the workflow and user privileges.

In some embodiments, user can provide sequence layout parameters. The sequence layout parameters include one or more of: bracket information, sequence header information, sample block information, and sequence footer information. In some embodiments, the bracket information includes one or more of: maximum samples per bracket, maximum brackets per sequence, number of alternate brackets, and use bracket block after sequence header.

Some embodiments further include running the generated workflow according to the defined sequence, and collecting resulting experimental data from the analytical laboratory instrument.

Furthermore, some embodiments include receiving input from an operator for an incomplete workflow, and updating the incomplete workflow with the received input. In some embodiments, input is a new analytical laboratory instrument.

Another aspect of the invention is a set of graphical user interfaces to assist a user in defining a sequence of analyses for an analytical laboratory instrument presented on a computer system with memory, a display, and one or more processors to execute one or more programs stored in the memory. The graphical user interface includes a first section presented on the display for receiving user inputs including changes to a lifecycle state of a workflow, wherein the lifecycle state is one of: workflow in development, workflow ready for use, workflow approved for use, and workflow retired. The graphical user interface also includes a second section presented on the display for receiving user inputs including workflow parameters, wherein the workflow parameters include one or more of: a workflow type, an instrument for which the sequence is to be defined, one or more methods that make up a sequence, and one or more associated files, wherein the user inputs define a sequence of analyses for an analytical laboratory instrument, the sequence of analyses being persistent for subsequent use.

In some embodiments, the graphical user interface includes a sequence setting section presented on the display wherein the sequence setting include one or more of: report definition, data presentation layout, preferred channel, sequence name, sequence location, and sequence description. Furthermore, in some embodiments, the graphical user interface includes a sequence layout parameters section presented on the display wherein the sequence layout parameters include one or more of: maximum samples per bracket, maximum brackets per sequence, number of alternating brackets, number of sequence headers, use of bracket block after the sequence header, sample block information, and sequence footer information. In some embodiments, the graphical user interface includes an option allowing a user to restrict use of the sequence to the analytical laboratory instrument for which it is defined.

Another aspect of the invention is a system for defining a sequence of analyses for an analytical laboratory instrument. The system comprises one or more central processing units, CPU(s), for executing programs and also includes memory sorting the programs to be executed by the CPUs. The programs include instructions to perform any of the embodiments of the aforementioned method. Such a system defining a sequence of analyses for an analytical laboratory instrument may also include program instructions to execute the additional options discussed above.

Yet another aspect of the invention involves embodiments of a computer readable storage medium storing one or more programs configured for execution by a computer to define a sequence of analyses for an analytical laboratory instrument. The programs include instructions to perform any of the embodiments of the aforementioned method. Such a computer readable storage medium may also include program instructions to execute the additional options discussed above.

BRIEF DESCRIPTION OF THE DRAWINGS

FIGS. 4A and 4B illustrate examples of graphical user interfaces (GUIs) for a workflow editor showing how the workflow editor can be accessed from the workflow application.

FIGS. 7A-7G illustrate examples of graphical user interfaces (GUIs) for a "sequence layout settings" of the workflow editor.

Like reference numerals refer to corresponding parts throughout the drawings.

DESCRIPTION OF EMBODIMENTS

According to some embodiments, methods, systems, and user interfaces are described for enabling a user to create workflows that can be used to generate sequences for analytical instruments according to regulations and Standard Operating Practices (SOPs). In some embodiments, a computer-implemented workflow application is provided that captures laboratory-specific rules that govern creation and modification of sequences for analytical instruments, such as chromatography sequences. Once the workflows are created (e.g., by an administrator having high privileges), a downstream user (e.g., an operator having low privileges) can generate sequences in accordance with the rules (e.g., laboratory rules), and while requiring minimal training and effort. In some embodiments, the generated sequences can be modified only in accordance with the rules, because rules that were applied during the creation of the workflow are permanently stored with the sequence. The workflow application routes tasks in a predetermined task execution sequence to one or more workers. In addition, the workflow application provides access to data and documents required by each worker to complete a particular task.

In some embodiments, a method for defining a sequence of analyses for an analytical instrument using a workflow includes receiving user inputs including workflow parameters for defining the sequence, and automatically defining the sequence for the analytical instrument based on the workflow parameters, including creating rules for the sequence. The rules are persistent for subsequent use of the sequence. The rules are defined by the user, e.g., an administrator, who creates or edits the workflow. In some embodiments, the administrator can leave some choices available to operators who run the workflow. Administrator authoring the workflow can set the configuration of the sequence columns that will be displayed for the operators and specify processing methods and data presentation layouts, so as to either display less information or to display a lot of information.

Figure 1:
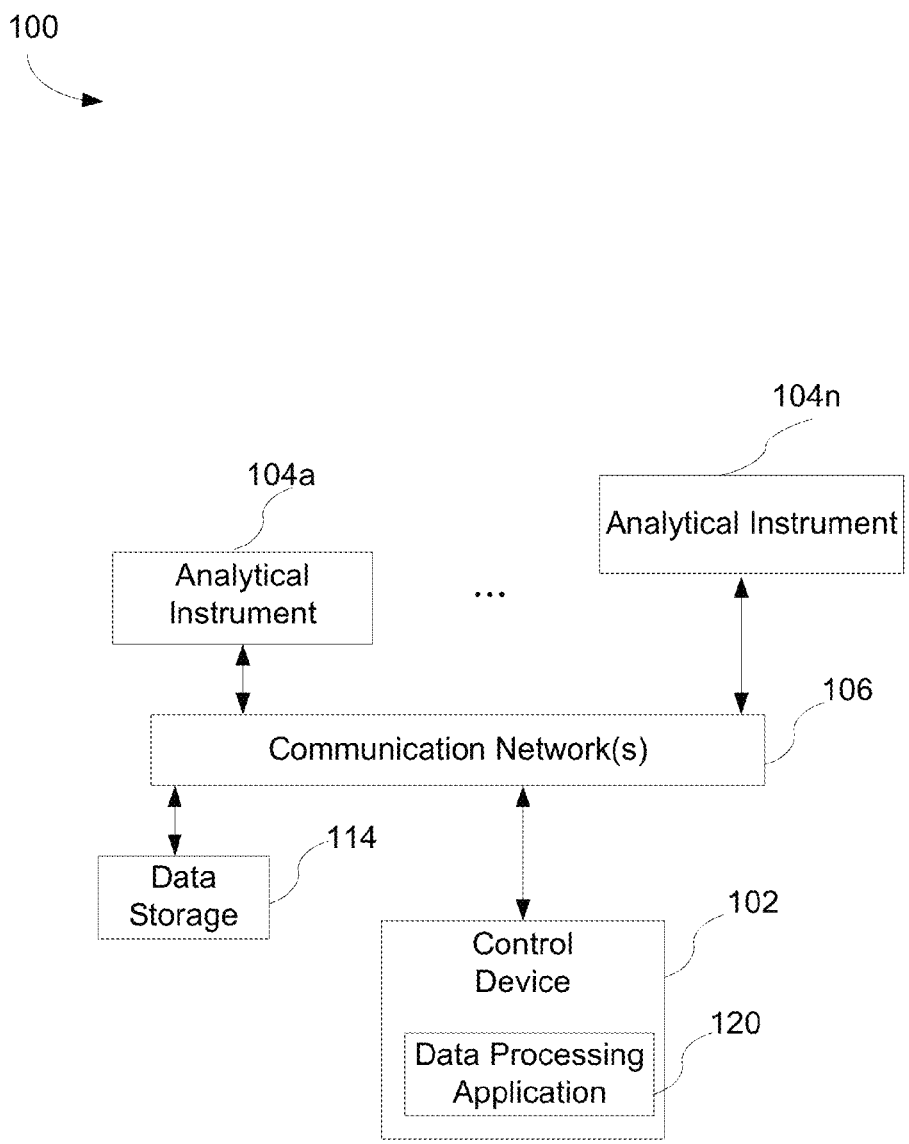
FIG. 1 illustrates an example of an analytical system according to some embodiments.

FIG. 1 is a block diagram of an analytical system 100. The analytical system 100 includes one or more analytical laboratory instruments 104 (such as a chromatography instrument) in communication with a control device 102 and a data storage device 114. Analytical laboratory instruments 104 may include: chromatography instruments, optical spectrometers, nuclear magnetic resonance spectroscopy (NMR) spectrometers, mass spectrometers, radioactivity detectors, refractive index detectors, light scattering detectors, and ultraviolet-visible spectroscopy (UV/Vis) detectors. Other detectors that can be used are described in U.S. Pat. No. 6,562,628 Entitled, "Electrolytic Suppressor and Separate Eluent Generator Combination," incorporated herein by reference. The control device 102 has stored thereon a data processing application 120 (such as a workflow chromatography application). The laboratory instruments 104, the data storage device 114 and the control device 104 may be in communication with each other using one or more communications network(s) 106 or may be connected to each other without using any communication network 106, such as by use of a USB, RS-232, IEEE, or LAN cable/connection. Communications network(s) 106 can be any of a number of networks (e.g. Internet, intranet, local area network, wide area network, wireless network, wired network, optical network, etc.). In some embodiments, executing on the control device 102 is a data processing application 120. An example of a data processing application 120 is Chromeleon Chromatography Management System, which is a trademark of Dionex Corporation of Sunnyvale, Calif.

Although FIG. 1 shows an analytical system, FIG. 1 is intended more as functional description of the various features. In practice, and as recognized by those of ordinary skill in the art, items shown separately could be combined and some items could be separated.

Figure 2:
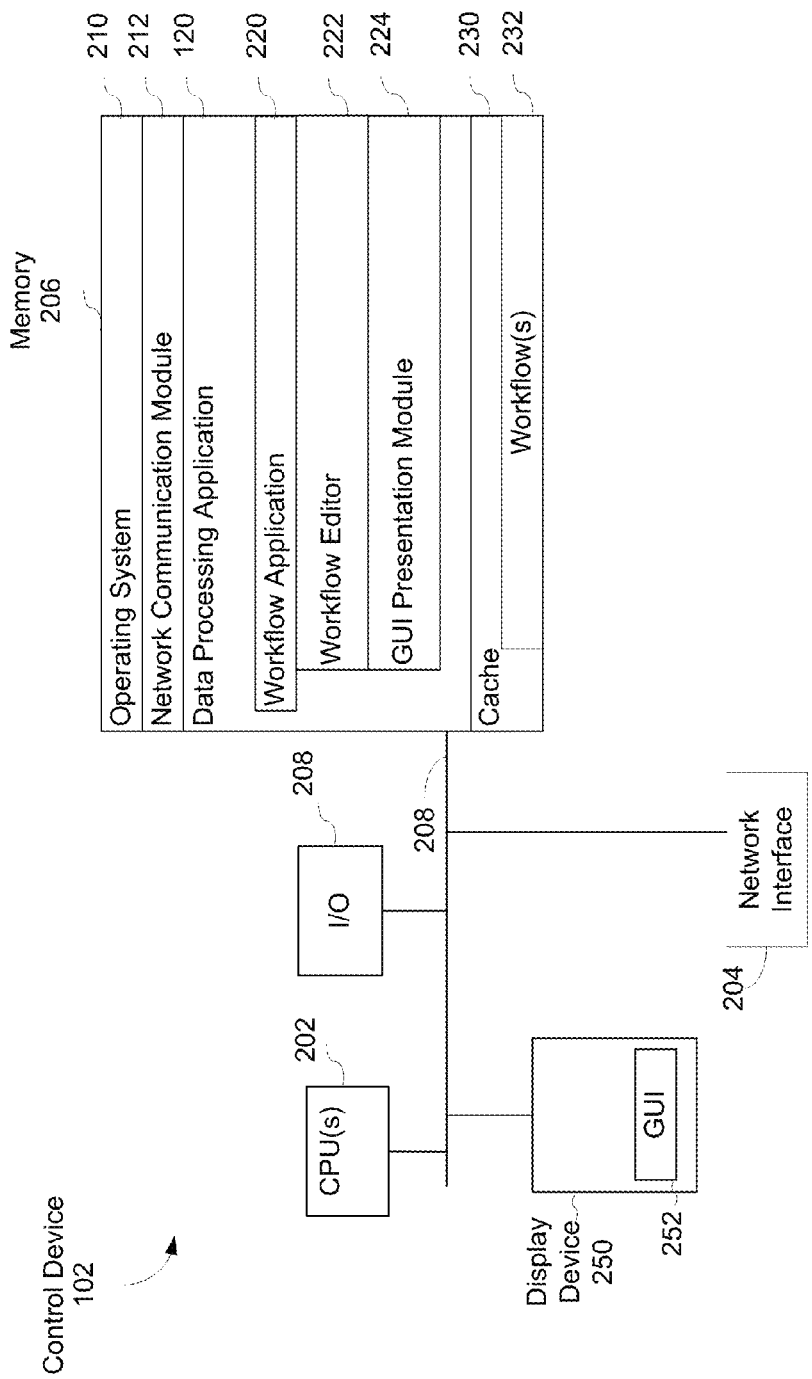
FIG. 2 is a block diagram illustrating a control device with a workflow application according to some embodiments.

FIG. 2 illustrates a block diagram of a control device 102. The control device 102 generally includes one or more processing units (CPU's) 202, one or more network or other communications interfaces 204, memory 206, an input device 208 (such as keyboard, mouse, and the like), an output device 250, such as a display device 250 and one or more communication buses 208 for interconnecting these components. The display device 250 may be used to render a user interface 252 (such as, a graphical user interface (GUI)) associated with the operation of the data processing application 120. The communication buses 208 may include circuitry (sometimes called a chipset) that interconnects and controls communications between system components. Memory 206 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the CPU(s) 202. Memory 206, or alternately the non-volatile memory device(s) within memory 206, comprises a computer readable storage medium. In some embodiments, memory 206 stores the following programs, modules and data structures, or a subset thereof:

- an operating system 210 that includes procedures for handling various basic system services and for performing hardware dependent tasks;
- a network communication module 212 that is used for connecting the control device 102 to other computers via the one or more communication network interfaces 204 (wired or wireless) and one or more communication networks, such as the Internet, other wide area networks, local area networks, metropolitan area networks, and so on;
- a data processing application 120 for measuring and evaluating experimental data, and including a workflow application 220 for enabling a user to create complex sequences according to regulations and requirements. The workflow application 220 includes a workflow editor 222 to enable a user to create a workflow, and a GUI presentation module 224 to present a graphical user interface (GUI). Workflows help a user to create sequences that exactly match requirements (such as, according to regulations and SOPs) without in-depth knowledge; and
- a data cache 230, for instance to store rules, workflows 232, sequence settings, method files, user preferences, and default settings, etc.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, memory 206 may store a subset of the modules and data structures identified above. Furthermore, memory 206 may store additional modules and data structures not described above.

Figure 3:
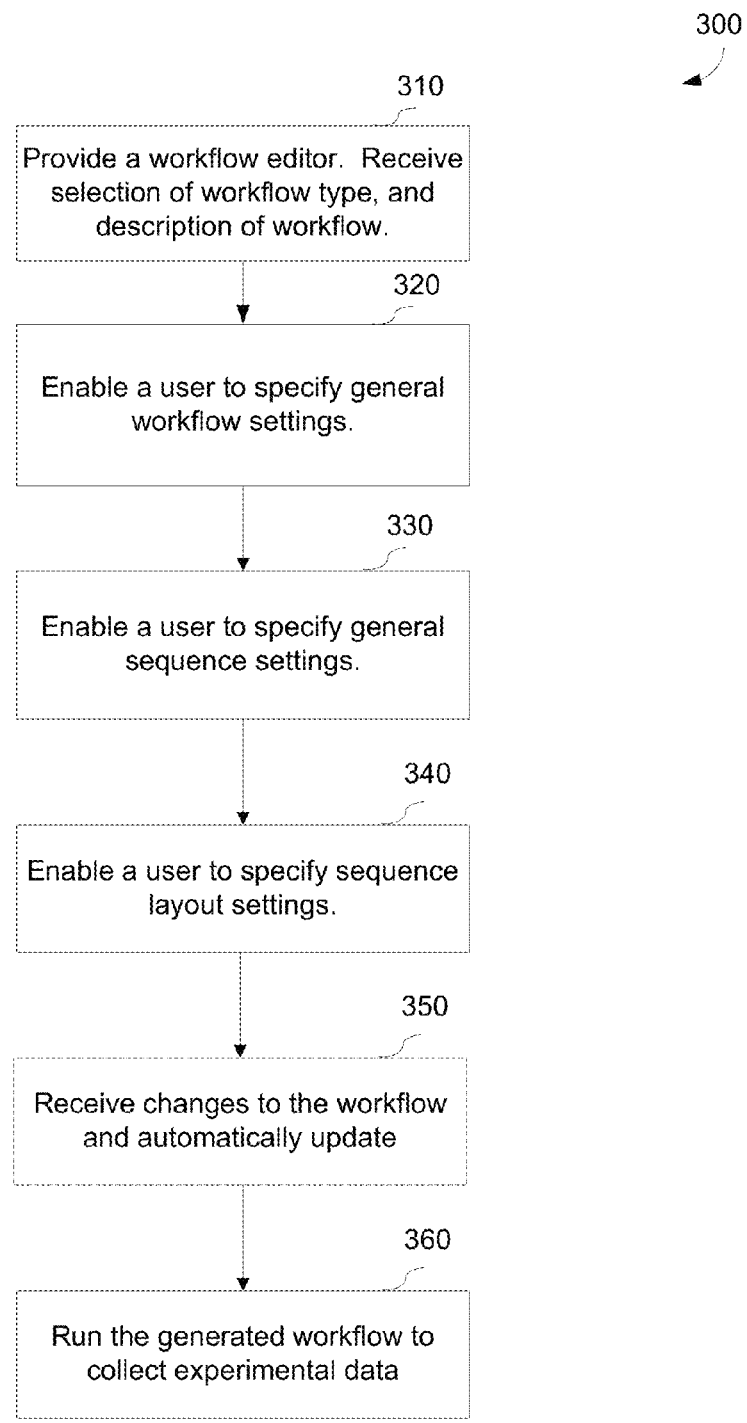
FIG. 3 is a flow diagram of a process performed by the workflow application to create, use, and edit a workflow according to some embodiments.

FIG. 3 is a flowchart representing a method 300 performed by the workflow application 220 for enabling an administrator to create, use, and edit a workflow, according to some embodiments. In general, in order to enable a user to create a workflow, the workflow application 220 provides a workflow editor 222 that requires completion of inputs for three sections in order, as described below.

In order to enable a user to generate a workflow, the workflow application 220 provides (310) a workflow editor 222, and receives user selection of a type of the workflow to be created and a user description of the workflow to be created. In some embodiments, the workflow editor 222 provides a list of workflow types (e.g., in a drop-down menu), such that the user creating the workflow can select a workflow type.

Figure 4A:
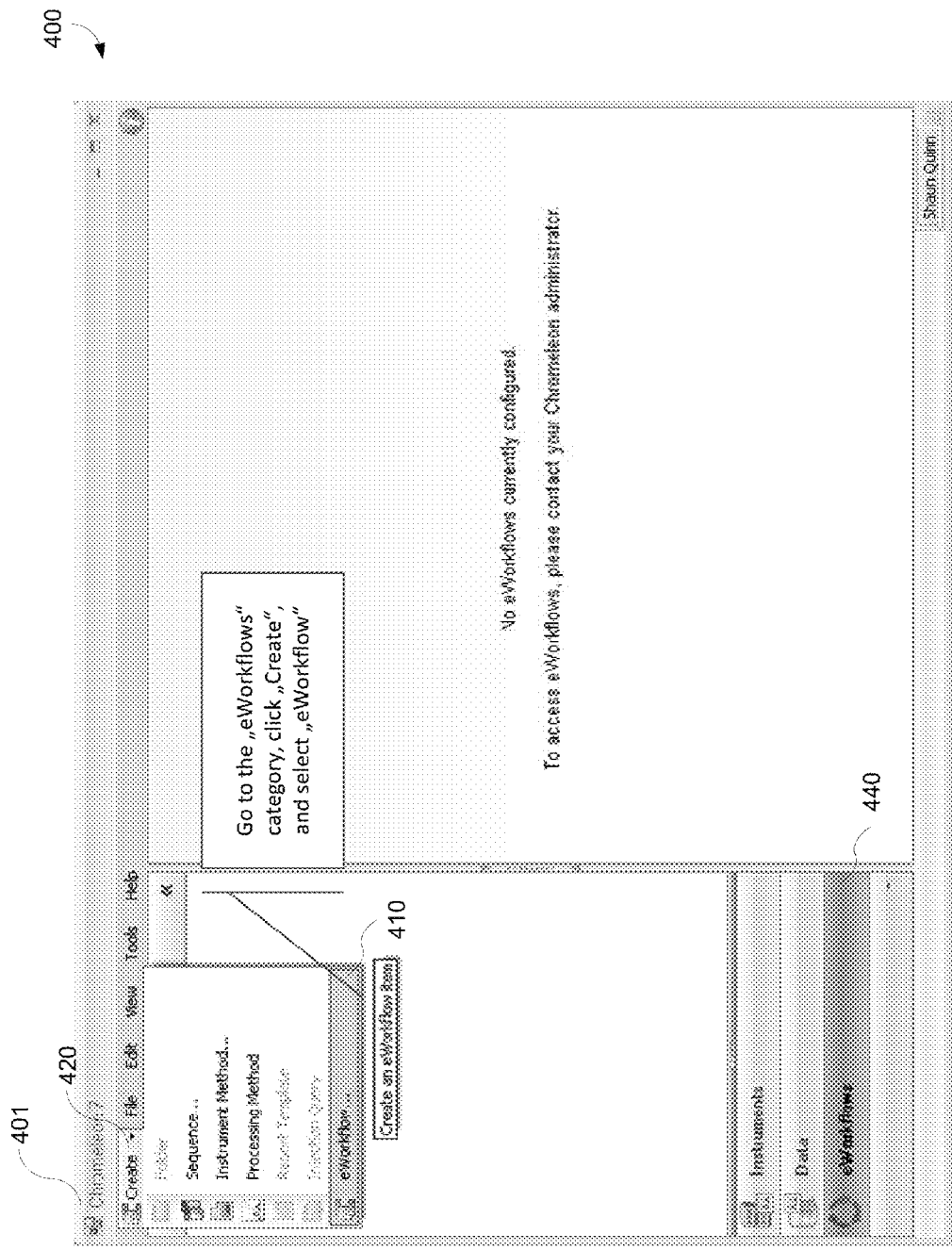

FIG. 4A illustrates an example of a graphical user interface 400 that may be presented to a user in order to invoke the workflow editor 222. A user can select a "Workflows" option 410 from a Create Toolbar 420, from within a Workflow pane 440 of the chromatography application 401. The Graphical User Interfaces of FIGS. 4A-9C are illustrated with a chromatography application 401, but in other embodiments using non-chromatography workflow applications is also possible. Typically, the user who creates (300) the workflow is an advanced user, such as a lab manager, with a high level of privileges.

Referring back to FIG. 3, in order to generate a workflow, the workflow editor 222 is split into three sections, each of which requires input from a user. First, the workflow editor 222 enables and requires the user to specify general workflow settings (320). Second, the workflow editor 222 enables and requires the user to specify general sequence settings (330). Third, the workflow editor 222 enables and requires the user to specify sequence layout settings (340). Some embodiments provide an option for receiving changes to the workflow parameters and automatically updating the workflow according to the changes (350). For example, some embodiments provide the option of receiving changes to the workflow parameters for defining the sequence and automatically updating the sequence based on the changes to the workflow parameters in accordance with the rules for the sequence. Once the workflow is generated, the user or another, potentially less skilled, operator, runs the generated workflow according to the defined sequence to collect experimental data from the analytical laboratory instrument (360).

FIG. 4B illustrates an example 450 illustrating the workflow editor 222, which contains three sections—workflow general section 460, sequence general section 470, and sequence layout section 480. The workflow general section 460 accepts inputs from a user regarding general workflow settings, while the sequence general pane 470 accepts inputs from the user regarding general sequence settings, and the sequence layout pane 480 accepts inputs from the user regarding sequence layout.

Figure 5:
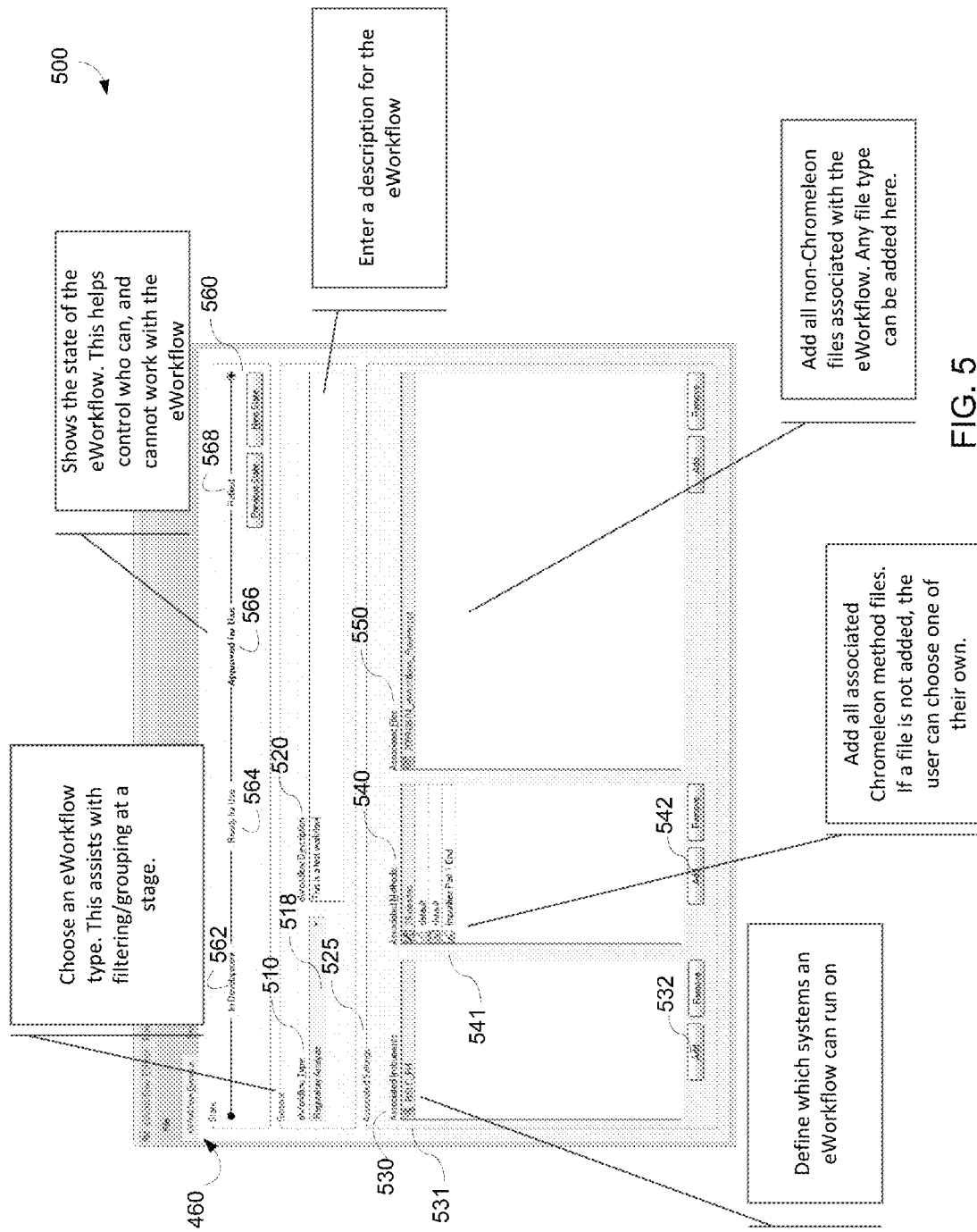
FIG. 5 illustrates an example of a graphical user interface (GUI) for a "workflow general pane section" of the workflow editor.

The operation 320 (FIG. 3) and the "Workflow general section" 460 are further described with reference to the GUI 500 illustrated in FIG. 5. As depicted in FIG. 5, a user chooses a workflow type 510. In some embodiments, the workflow editor 222 provides a drop down menu 518 from which the user can select a desired workflow type 510. In the example illustrated in FIG. 5, the user has selected a workflow type of "regulatory analysis" 518. In some embodiments, the user can also define a new/custom workflow type. Accordingly, a user can define the workflow, or the workflow can be predefined according to regulatory (e.g., US, EP, or EPA) methods and be included in the workflow application 220. Selecting a workflow type can assist with filtering and/or grouping during later stages. The user can also enter a workflow description 520.

The workflow application 220 defines one or more settings 525 associated with the workflow type 510. For instance, the workflow application 220 provides a list of suitable instruments 530 on which a workflow having an associated workflow type 510 can run, for instance in a drop down menu. A user can select one or more of the instruments 531 provided in the list and add them using the Add button 532. A user can also add one or more other instruments that are not listed in the list provided by the workflow application 220, for instance if the list is empty. In some embodiments, use of the sequence is restricted to the analytical laboratory instrument for which it is defined. In some embodiments, the user can only add those instruments that are accessible to the user based on the user's account privileges. The workflow application 220 provides a list of associated instrument method and processing method files 540, for instance in a drop down menu. A user can select one or more of the listed method files 541 and add them using the Add button 542. A user can also add one or more method files that are not listed in the list provided by the workflow application 220, for instance if the list is empty. A user can also optionally add one or more other files associated with the workflow in a portion 550 of GUI 500, so that these files will be available for the user for reference purposes. The user can add any type of files (e.g., text documents, power points, pdfs, etc.). Files can either be added directly or added as a link. One benefit of adding a link is that multiple workflows can use the same file, and that subsequent modifications to that file immediately apply to all associated workflows.

Also illustrated in the GUI 500 is a bar 560 that shows a state of the workflow. A workflow can be in one of four states: "In Development" 562, "Ready for Use" 564, "Approved for Use" 566, and "Retired" 568. "In Development" 562 refers to a workflow state in which the workflow is still being developed. "Ready for Use" 564 refers to a workflow state in which the workflow is ready has been created, but has not been approved. For instance, if the user creating the workflow does not have enough authority, the workflow may need to be approved, for instance, by a user having higher authority, such as a lab manager. "Approved for Use" 564 refers to a workflow state in which the workflow is ready has been created and has been approved (if required). At this state, the workflow can be used to generate sequences by users with appropriate privileges. "Retired" 568 refers to a workflow state in which the workflow has been retired. In some embodiments, the user creating the workflow can provide user inputs to change the lifecycle state of the workflow. In some embodiments, the workflow editor 222 updates the lifecycle state of the workflow without explicit user input. In some embodiments, user inputs such as "workflow in development," "workflow ready for use," "workflow approved for use," and "workflow retired" are received. The lifecycle state of the workflow is automatically updated based on the changes. Use of the sequence based on the lifecycle state of the workflow and user privileges is then permitted.

Figure 6:
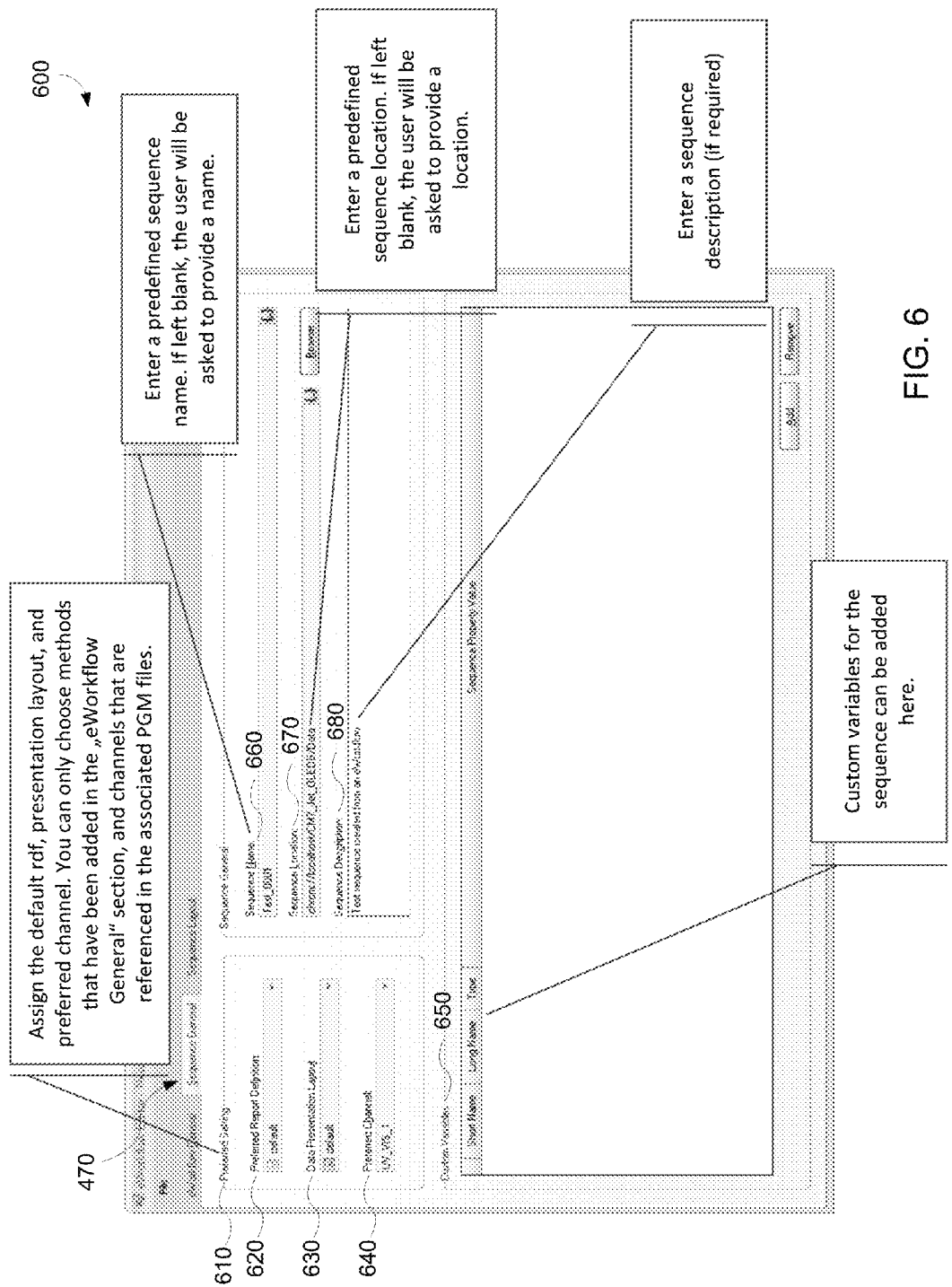
FIG. 6 illustrates an example of a graphical user interface (GUI) for a "sequence general pane" of the workflow editor.

The operation 330 (FIG. 3) and the "Sequence General section" 470 are further described with reference to the GUI 600 illustrated in FIG. 6. As depicted in FIG. 6, the workflow editor 222 enables the user to assign preferred settings 610 for a sequence, including assigning a preferred report definition 620, a data presentation layout 630 and a preferred channel 640. The workflow editor 222 provides choices to the user for the preferred settings 610 based on the methods 540 added in the "workflow general" pane 460 shown in FIG. 5 and channels that are referenced in the associated files. The workflow editor 222 enables the user to add custom variables 650 for the sequence. The workflow editor 222 also requires input for some general information for the sequence, such as sequence name 660, sequence location 670, and sequence description 680. The workflow editor 222 provides a predefined sequence name or enables the user to provide a sequence name if no predefined sequence name is provided. The workflow editor 222 provides a predefined sequence location or enables the user to provide a sequence location if no predefined sequence location is provided.

Figure 7A:
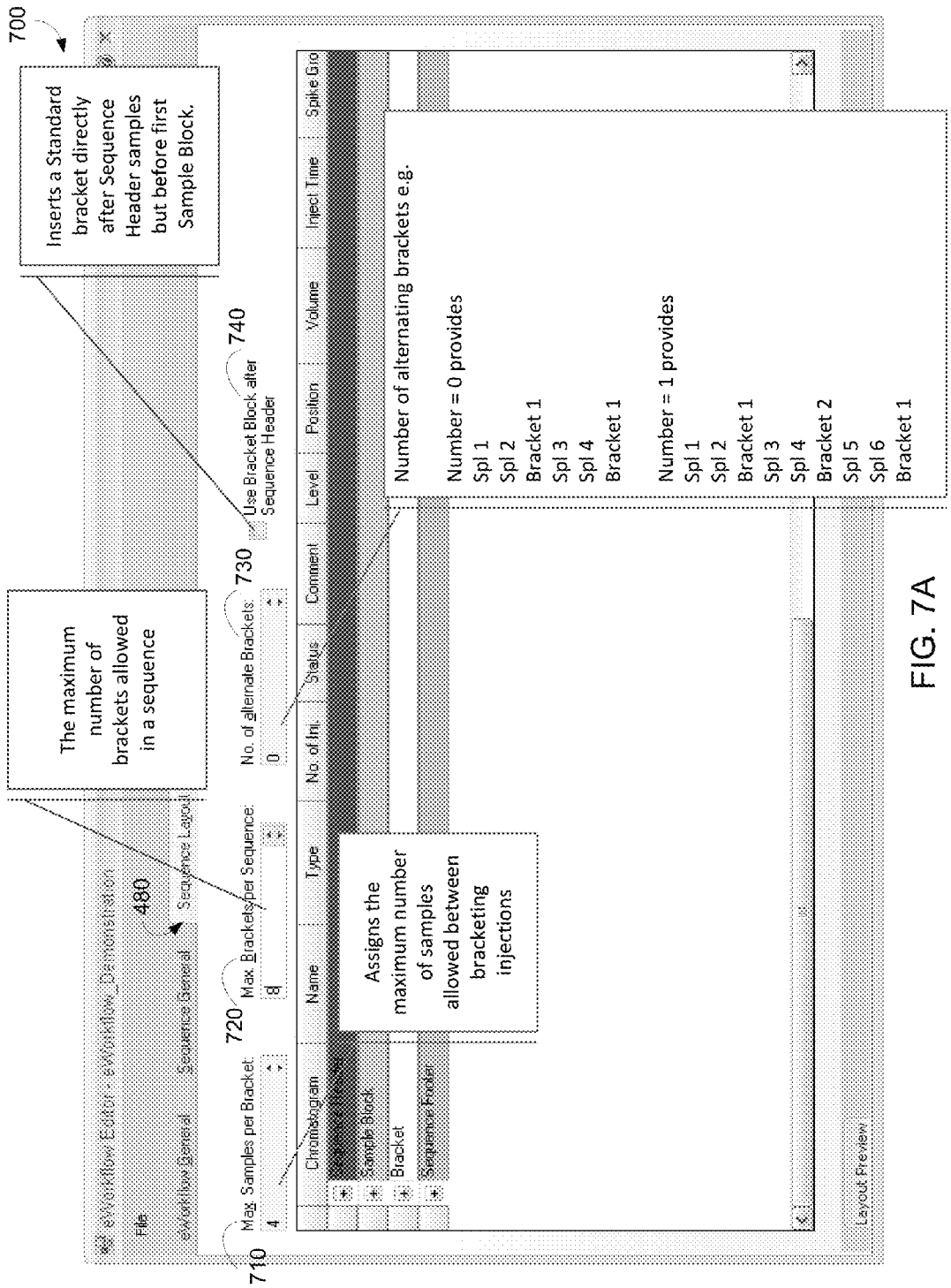
Figure 7B:
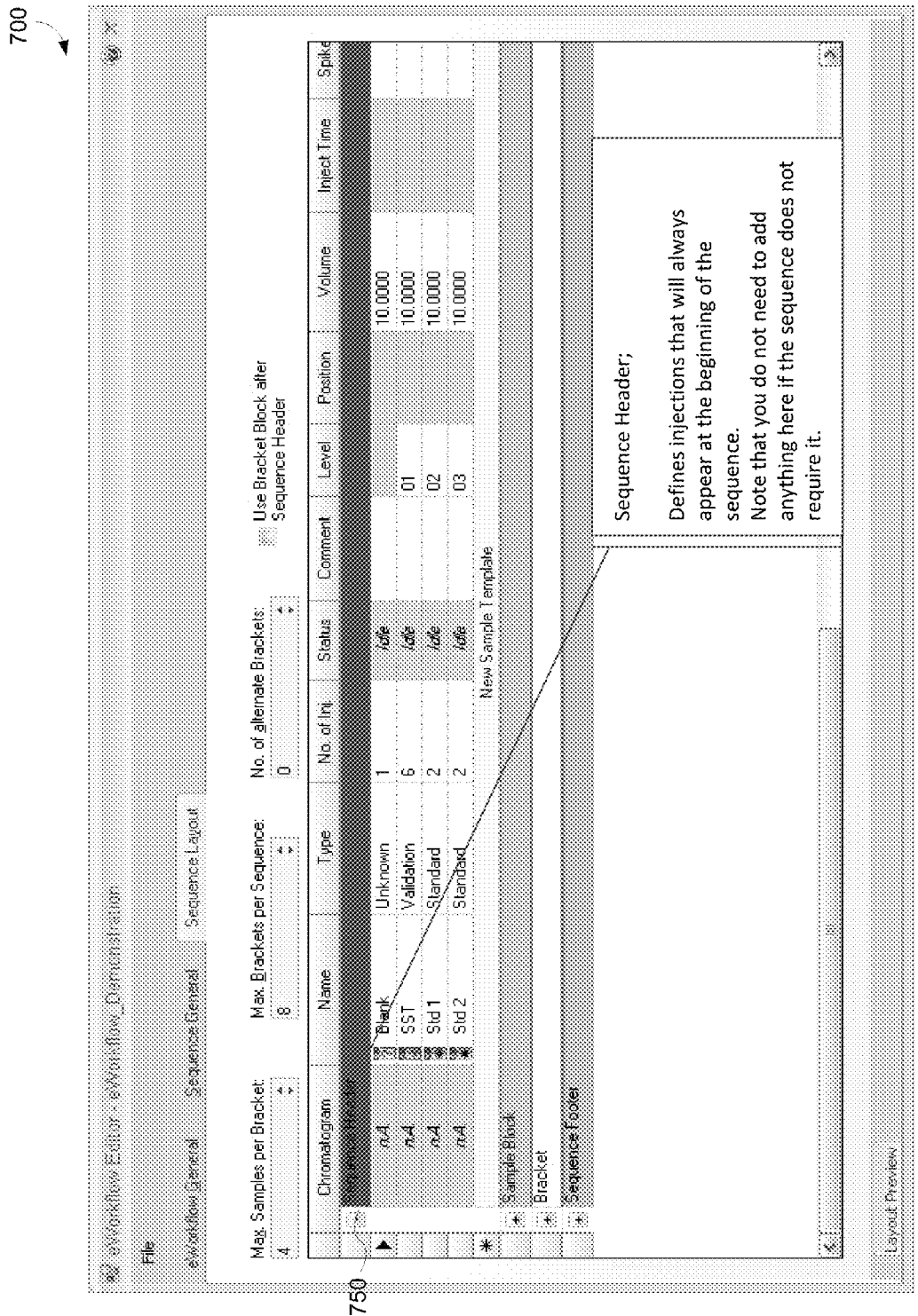
Figure 7C:
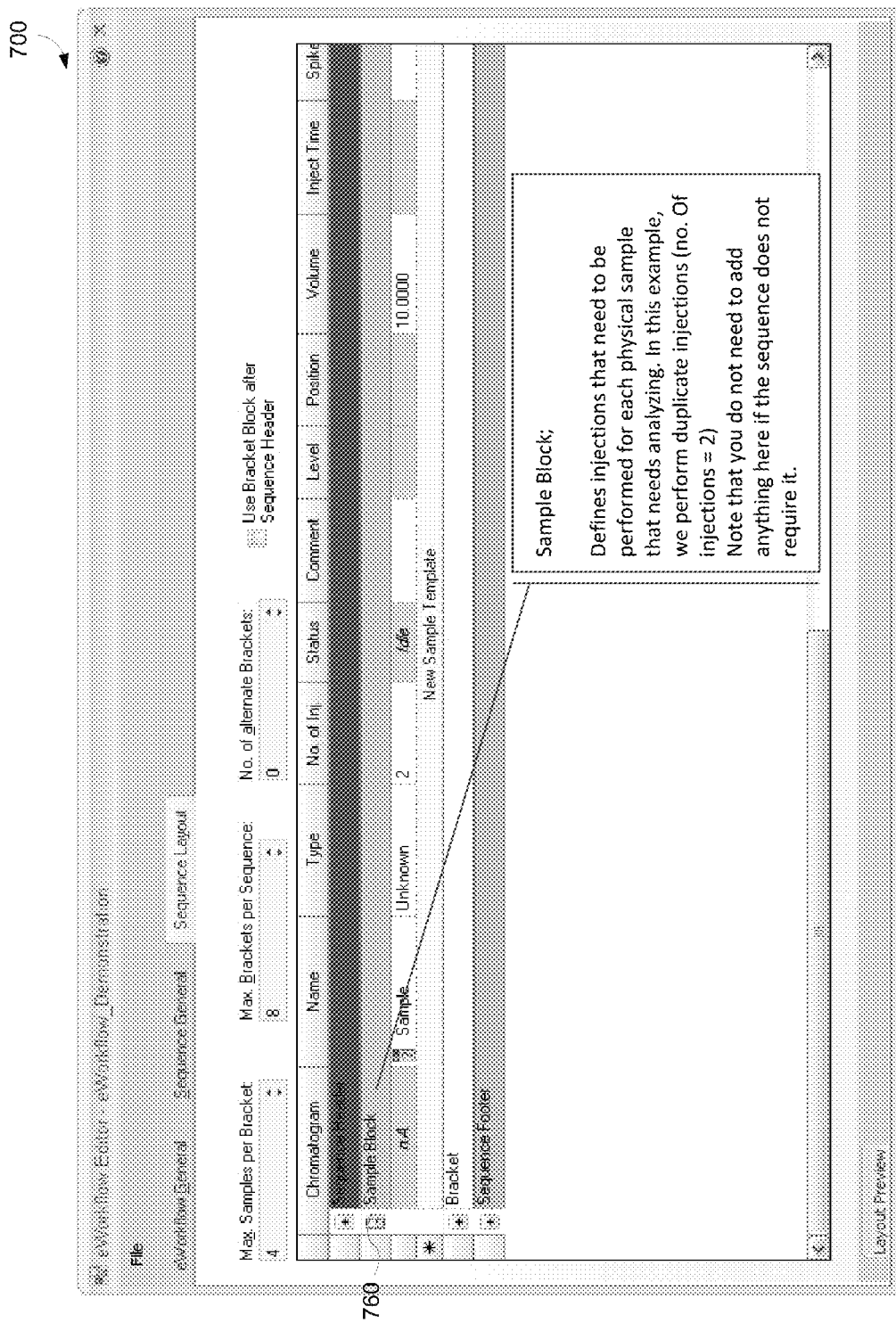
Figure 7D:
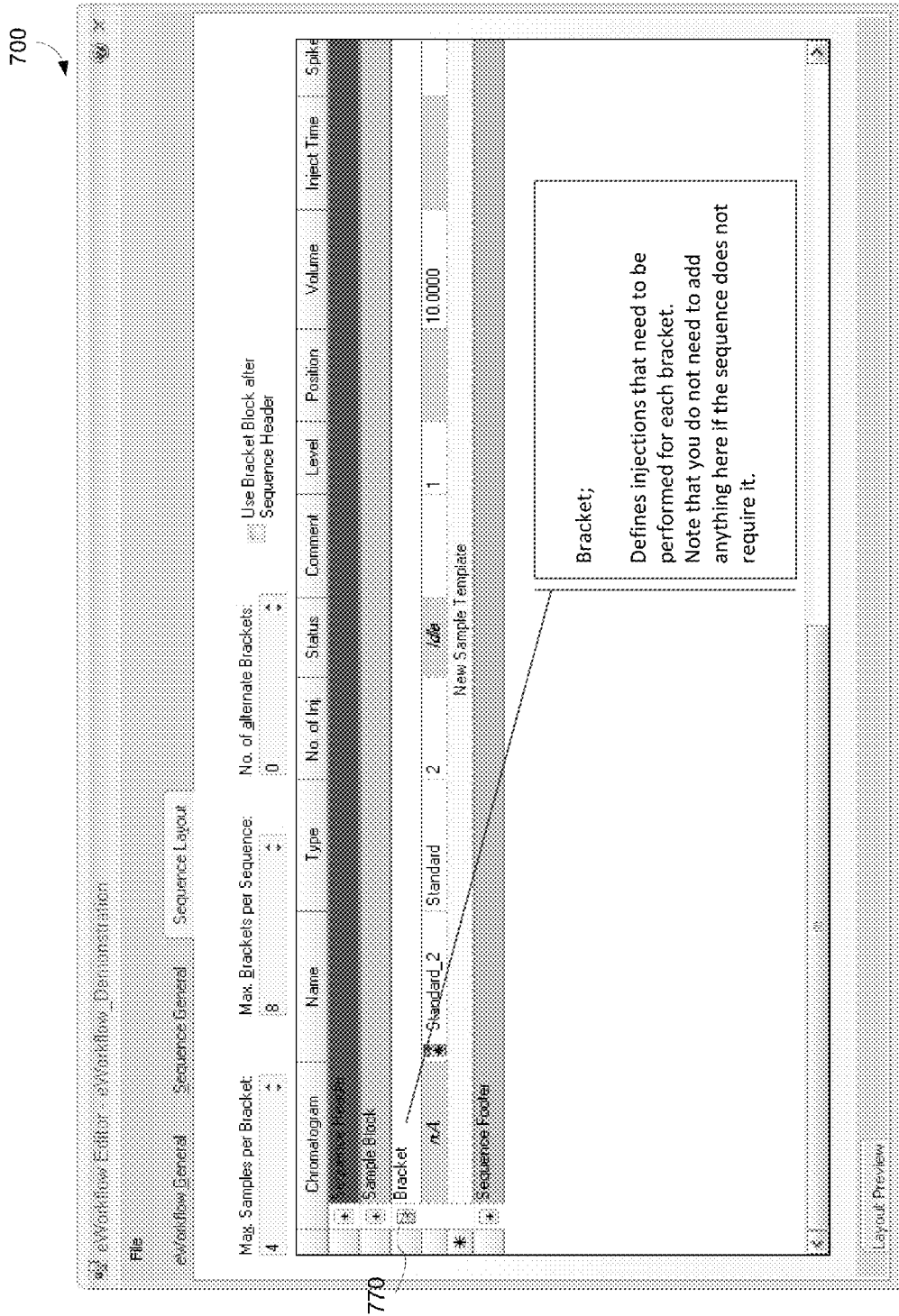
Figure 7E:
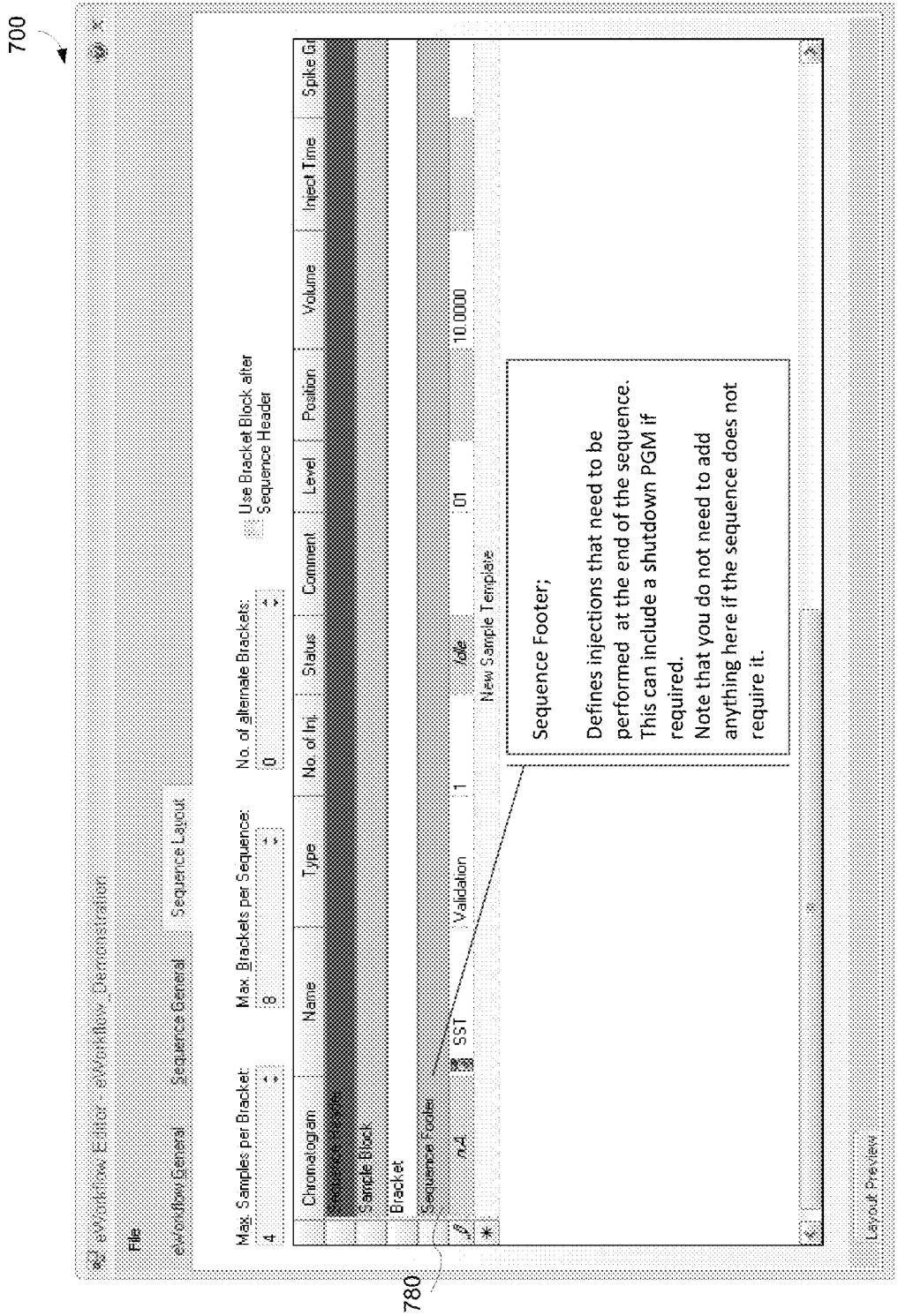
Figure 7F:
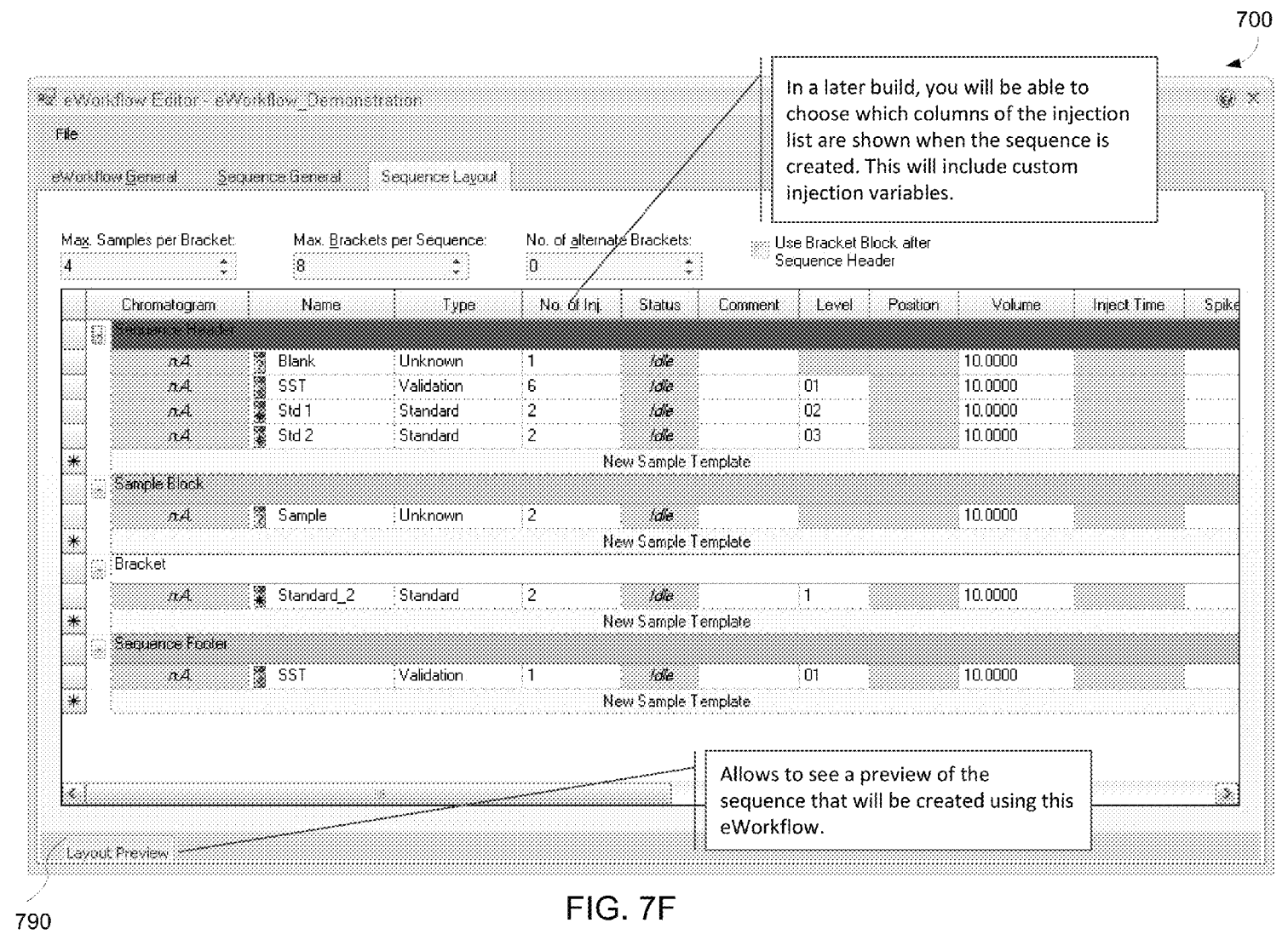
Figure 7G:
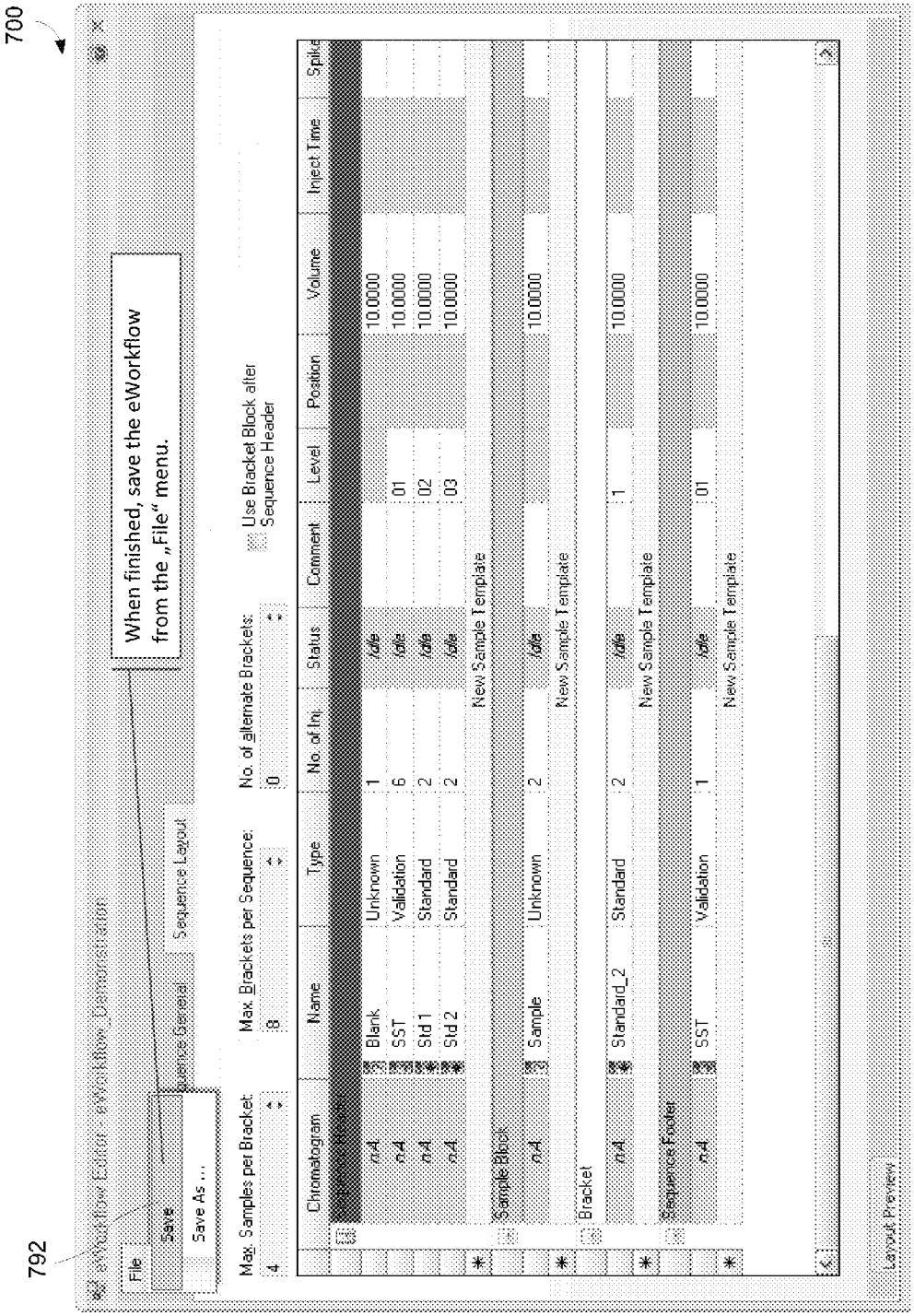

The operation 340 (FIG. 3) and the "Sequence Layout Settings section" 480 are further described with reference to the GUI 700 illustrated in FIGS. 7A-7G. As depicted in FIG. 7A, the workflow editor 222 enables the user to assign the maximum number of samples allowed between bracketing injections 710, the maximum number of brackets allowed in a sequence 720, a number of alternating brackets 730, and to indicate whether a standard bracket is to be inserted directly after sequence header samples but before a first sample block 740. As depicted in FIG. 7B, the workflow editor 222 enables the user to add one or more sequence headers 750 for the sequence, if required. A sequence header defines injections that will always appear at the beginning of the sequence. As depicted in FIG. 7C, the workflow editor 222 enables the user to add a sample block 760 for the sequence, if required. A sample block defines injections that need to be performed for each physical sample that needs analyzing. In the example depicted in FIG. 7C, because the number of injections is specified as two, duplicate injections are performed. As depicted in FIG. 7D, the workflow editor 222 enables the user to add a bracket 770 for the sequence, if required. A bracket defines injections that need to be performed for each bracket. As depicted in FIG. 7E, the workflow editor 222 enables the user to add a sequence footer 780 for the sequence, if required. A sequence footer defines injections that need to be performed at the end of the sequence. As illustrated in FIG. 7F, the GUI 700 also includes a "Layout Preview" option 790, which can be used by the user to see a preview of the sequence that will be created using this workflow. As illustrated in FIG. 7G, the GUI 700 includes a "Save" option 792, which can be used by the user to save the workflow.

Thus, in accordance with the methods and GUIs discussed with reference to FIGS. 3-7, a workflow can be created. Once the workflow has been created (FIGS. 3-7), it can be executed to create sequences that exactly match requirements (e.g., laboratory requirements). When the workflow is executed, it encodes data fields based on formulas that are evaluated in order to encode the structure of a sequence in terms of the required injections including type, volume, instrument method, processing method and any other parameter, such as user defined parameters. If any of the fields remains empty (i.e., the workflow is incomplete), the user is asked to provide the missing information when the workflow is executed, as discussed further with respect to FIGS. 9A-9C.

Thus, the workflow application 220 encodes the rules and requirements and the intelligence of the lab manager into software so that the user, such as a low level operator, can work according to these requirements without having to think about them. Workflows also allow more flexibility than copy paste templates while at the same time ensuring better compliance. Further, it is possible to embed or reference any document to the workflow, including documents to add guidance in order to actively assist the user when performing an analysis. All of this can improve ease-of-use, reduce training needs, and speed up data processing times.

FIGS. 8A-8E illustrate how a complete workflow that defines all required parameters can be used by an operator to generate sequences. Generally speaking, all required methods (e.g., associated methods 540, FIG. 5) are copied into a new sequence, either from the workflow directly or from a location defined by the workflow. The generated sequence is stored at a location (e.g., sequence location 670, FIG. 6) that is defined in the sequence general settings pane 470 of the workflow. The path and name of the sequence can be generated using built in variables such as, user name, date, time or name of the workflow. A list of injections can be built and filled in automatically according to the settings in the sequence layout pane 480 of the workflow. As the workflow knows how to generate the sequence, e.g., how many sample injections may be placed before a standard has to follow, it can build the sequence according to the rules independent of the number of samples to be analyzed. The rules are embedded into the generated sequence so that even after creation of the sequence it cannot be manipulated outside of the given requirements.

The sequence structure is defined by a header, brackets, a sample block and a footer, all of which can contain several injections of different types. Each block can be empty. Header and footer will always be placed at start and end of the sequence. The brackets alternate with the sample blocks as defined by the workflow. This includes a rule after how many samples a bracket must follow and whether the brackets can be equal throughout the sequence or must alternate themselves. With the given scheme it can be possible to create any sequence structure.

The required instrument method, processing method, view settings end report template can be either directly copied from the workflow and will then be copied from there into the new sequence or these objects can be referred to as links. In this case the object gets copied from the given location when the workflow is executed. This allows combining updated methods and templates from a central location with any Workflow. In addition to the required objects any user defined attachment, such as a PDF or Word file can be added or linked in the same way so that these files will be available for the user for reference purposes as well.

Figure 8A:
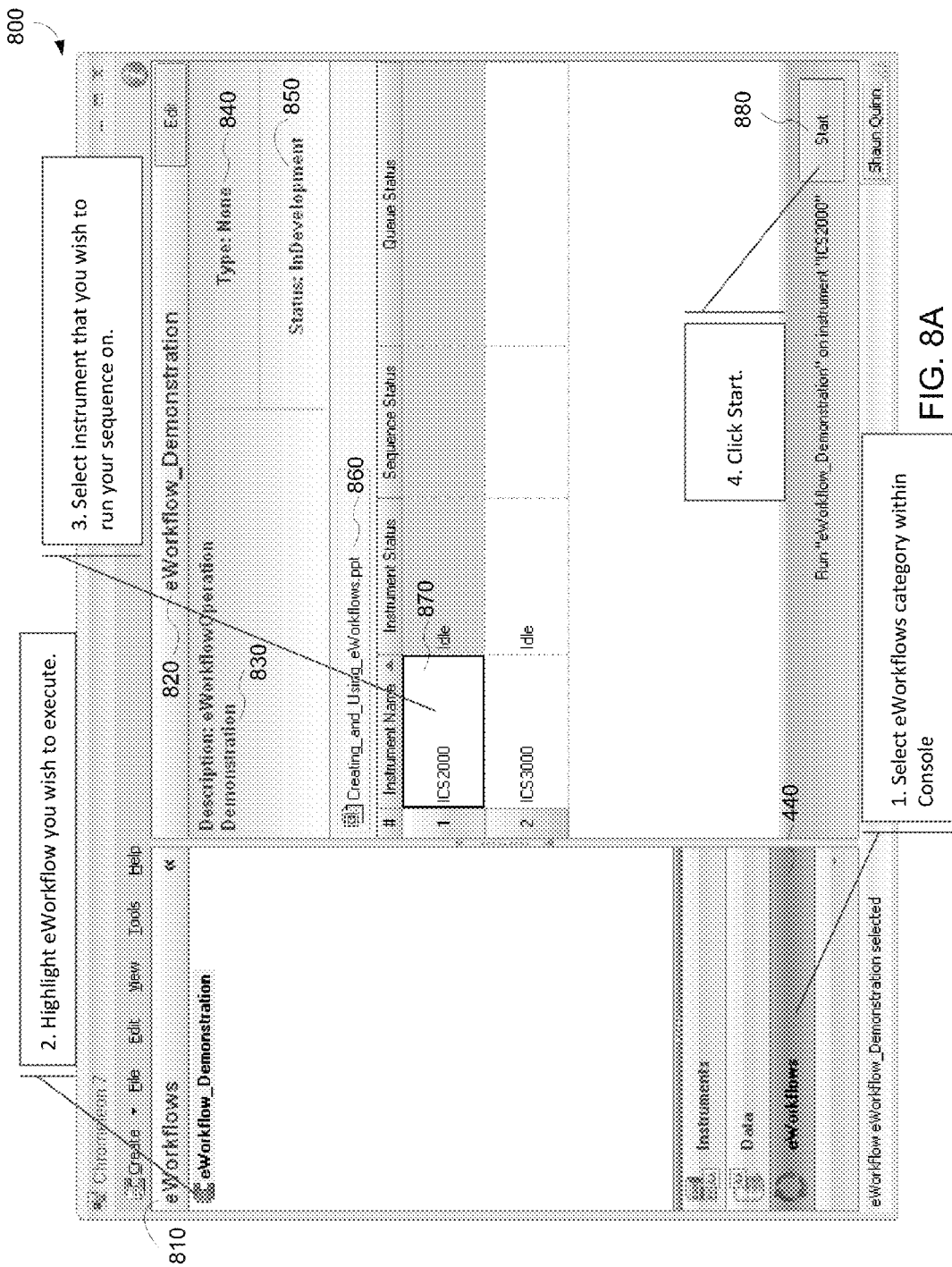
FIGS. 8A-8E illustrate examples of graphical user interfaces (GUIs) showing how a complete workflow can be used to create a sequence.

FIG. 8A illustrates a GUI 800 that is the same as GUI 400 (FIG. 4), except that here because a workflow has been created, it appears in a pane 810 from which a user can select it. Upon selecting the workflow titled "eWorkflow_Demonstration," from pane 810, some general description of the workflow appears in section 820 of the GUI 800. The general description includes a description 830 of the workflow (e.g., corresponding to the user-entered description 520), a workflow type 840 (e.g., corresponding to the user-specified workflow type 510), a workflow status 850 (e.g., corresponding to one of the user-entered workflow statuses 560), files associated with the workflow 860 (e.g., corresponding to the user-added associated files 550), and one or more associated instruments 870 (e.g., corresponding to the associated instruments 530). As discussed with reference to FIG. 5 above, the user can open the files 860 associated with the workflow before creating a sequence using the workflow, for instance by double-clicking.

FIG. 8A further shows that a user has selected the workflow editor 222 by selecting the workflow pane 440 provided by the data processing application 120, and has selected a workflow "eWorkflow_Demonstration" from pane 810, for instance by highlighting the workflow, double-clicking on it, etc. From the list of instruments 870 provided on which the sequence (that will be created) can run, the user can select an instrument that the user wishes to run the sequence on. In the example illustrated in FIG. 8A, the user has selected the instrument that has the name—"ICS2000." When the user presses the start button 880, an indication is sent to the workflow application 220 to run the workflow "eWorkflow_Demonstration" on instrument "ICS2000." In response to receiving the indication, the workflow application 220 starts up a procedure wizard, as described below.

Figure 8B:
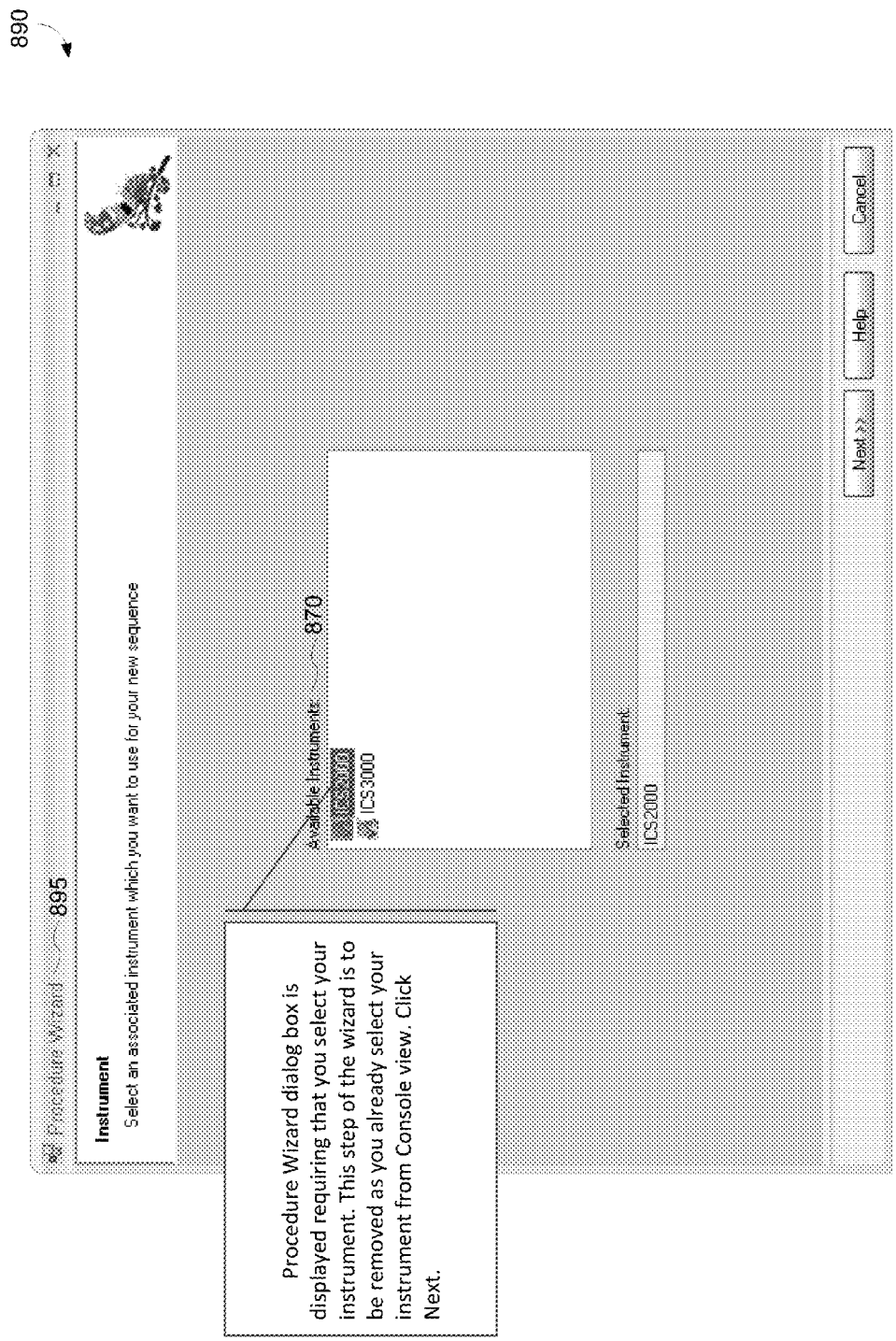

FIG. 8B illustrates an example of a GUI 890 that is displayed to the user if the user presses the start button 880 without selecting an instrument on which the user wishes to run the sequence from the lists of instruments 870. A wizard 895 displays the list of instruments 870 and requests that the user select an instrument from the displayed list. In the example illustrated in FIG. 8B, the user has selected the instrument that has the name—"ICS2000."

Figure 8C:
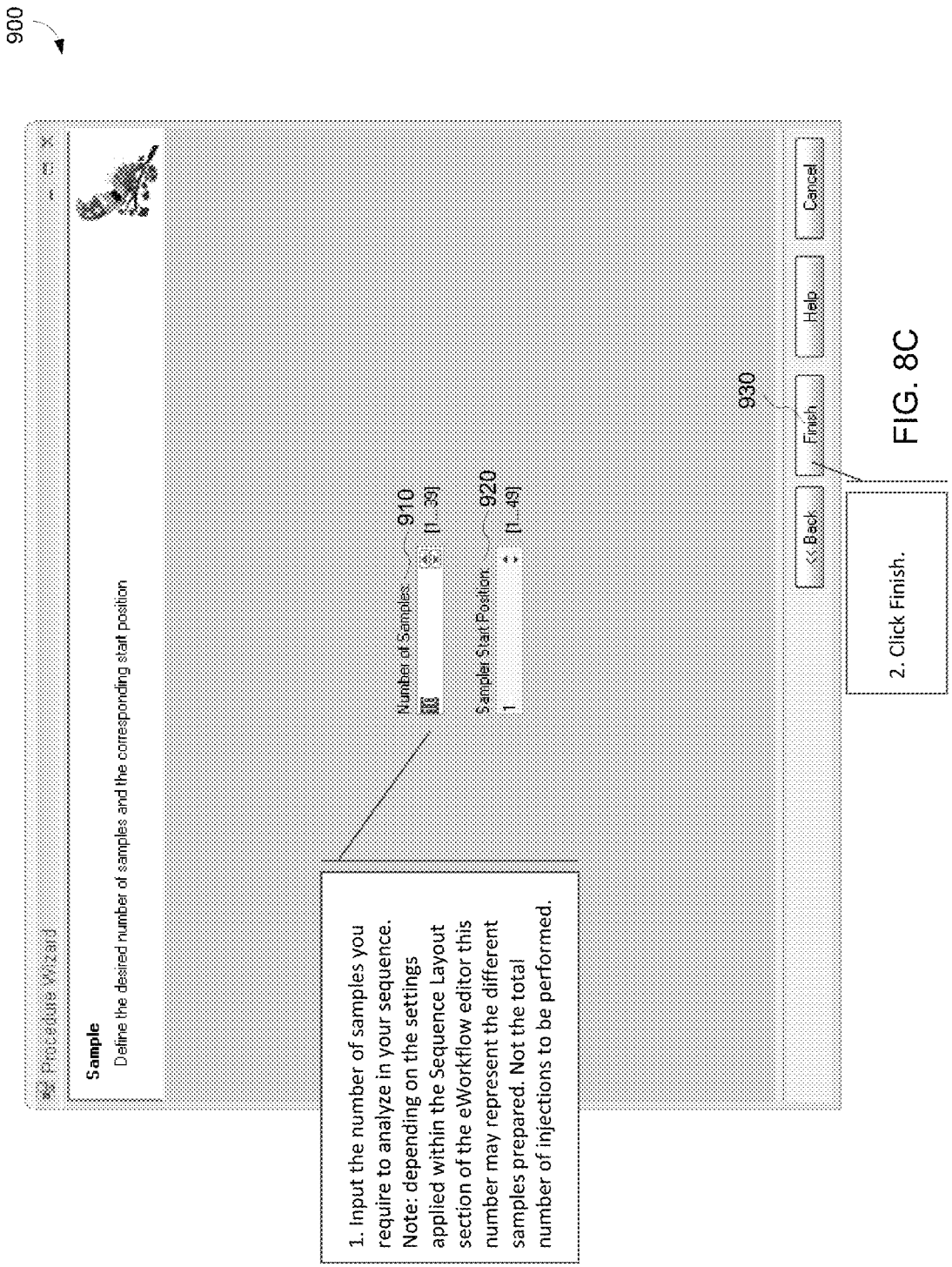

Once the user has selected an instrument on which to run the sequence, the wizard 895 causes display of a GUI 900, as illustrated in FIG. 8C. The GUI 900 provides an input area 910 in which the user inputs the desired number of samples the user requires to analyze in the sequence. In the example illustrated in FIG. 8C, the user has input that 10 samples are required. GUI 900 provided an input area 920 in which the user inputs the corresponding start position of the sampler. In the example illustrated in FIG. 8C, the user has specified a start position of 1. When the user presses the finish button 930, the sequence is created.

Figure 8D:
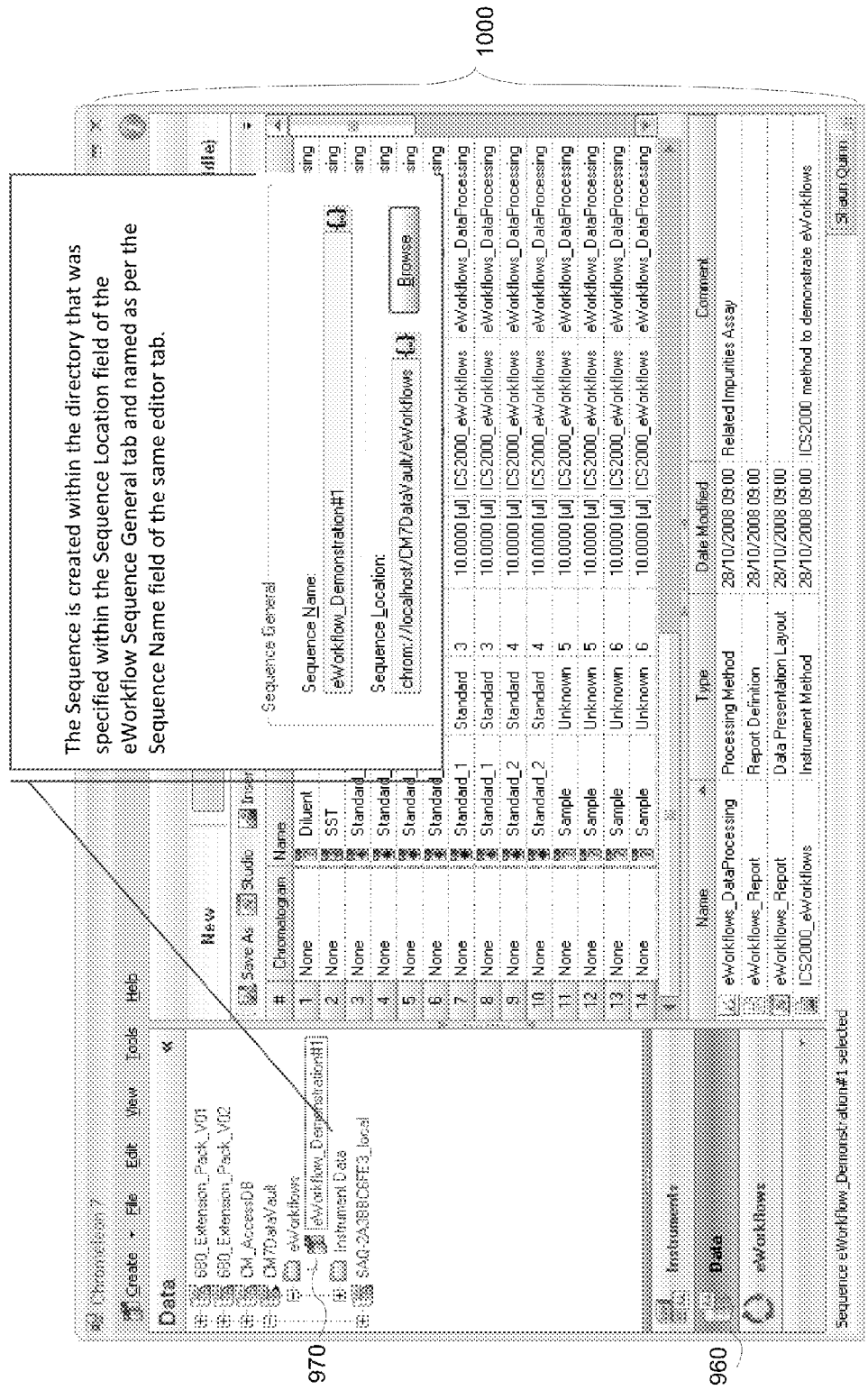

As illustrated in FIG. 8D, in some embodiments, the user can view the created sequence 1000 by accessing a Data pane 960 provided by the data processing application 120. The sequence "eWorkflow_Demonstration#1" is created within the directory 970 that was specified within the sequence location field 670 of the sequence general pane 470, and is named per the sequence name field 660 of the sequence general pane 470 (FIG. 6). The sequence 1000 is discussed further with respect to FIG. 8E showing a GUI 999.

Figure 8E:
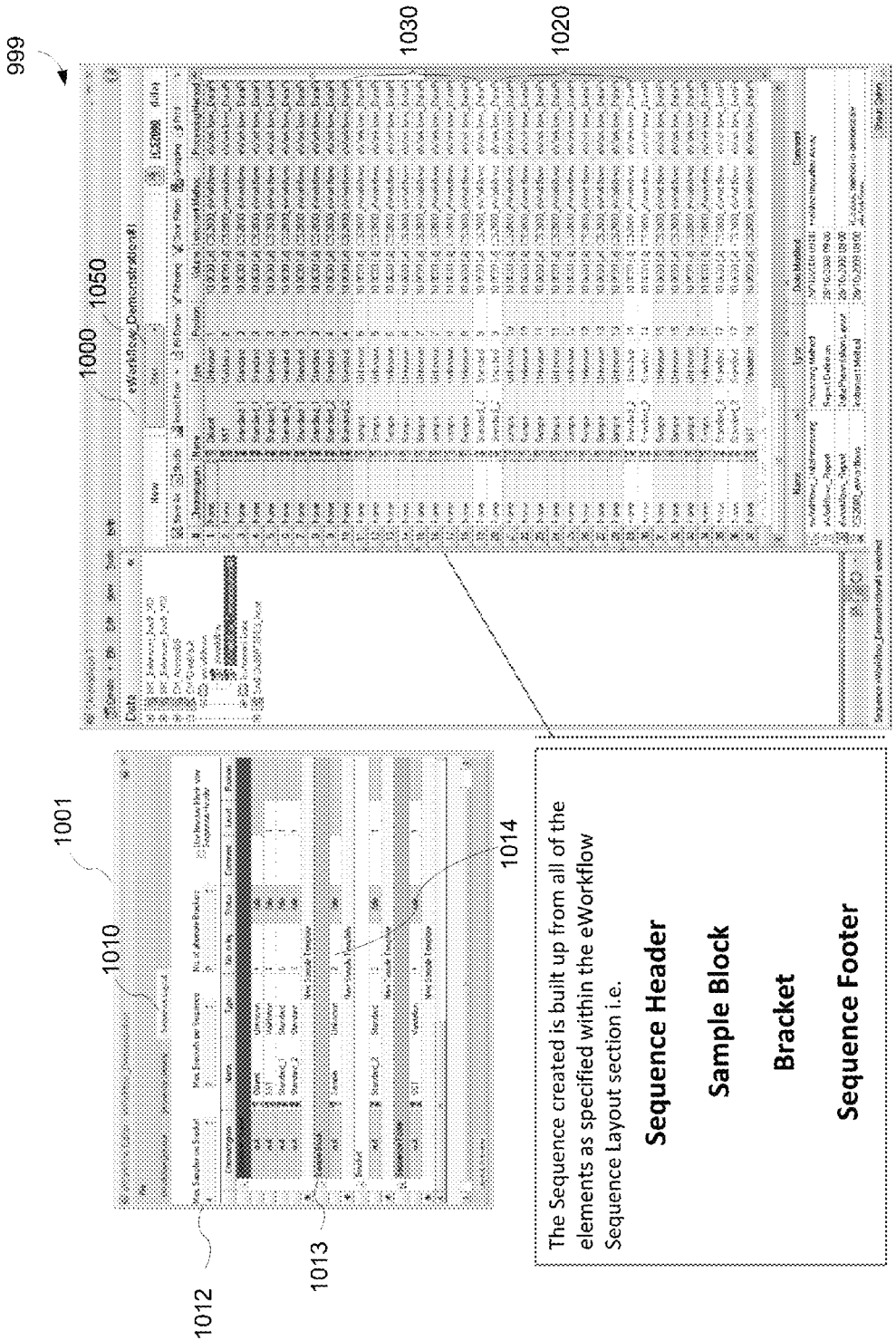

As illustrated in FIG. 8E, the sequence 1000, called "eWorkflow_Demonstration#1," is built up from all the elements as specified within the sequence layout pane 480. For ease of illustration, a GUI 1001 showing an example sequence layout pane 1010 is shown next to the GUI showing the sequence 1000. The sequence layout pane 1010 has four primary elements: sequence header, sample block, bracket, and sequence footer. These four are the primary elements that make up the sequence 1000. For instance, as can be seen in sequence layout pane 1010, the maximum number of samples per bracket 1012 is specified as 4. Further, the sample block section 1013 specifies that one sample is injected twice per sample block 1014. This effectively specifies duplicate injections per sample block. The result is a maximum of 8 injections within each sample block. Accordingly, sample blocks 1020 and 1030 of the sequence 1000 contain a maximum of 8 injections each.

The user can select the Start button 1050 to start the sequence 1000 once the instrument ICS2000 is ready. The sequence 1000 is added the sequence to the instrument queue.

Figure 9A:
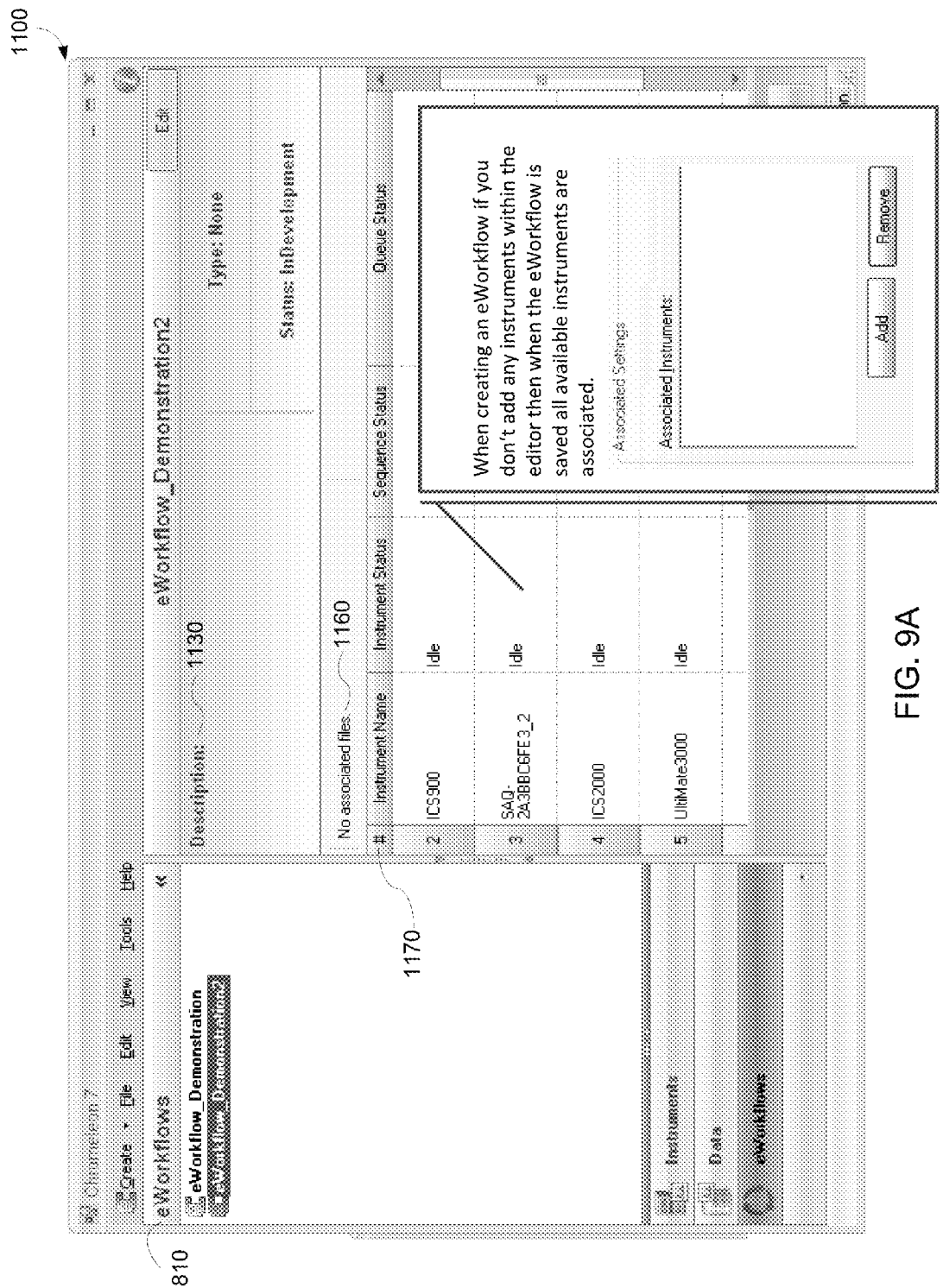
FIGS. 9A-9C illustrate examples of graphical user interfaces (GUIs) showing how an incomplete workflow can be completed.
Figure 9B:
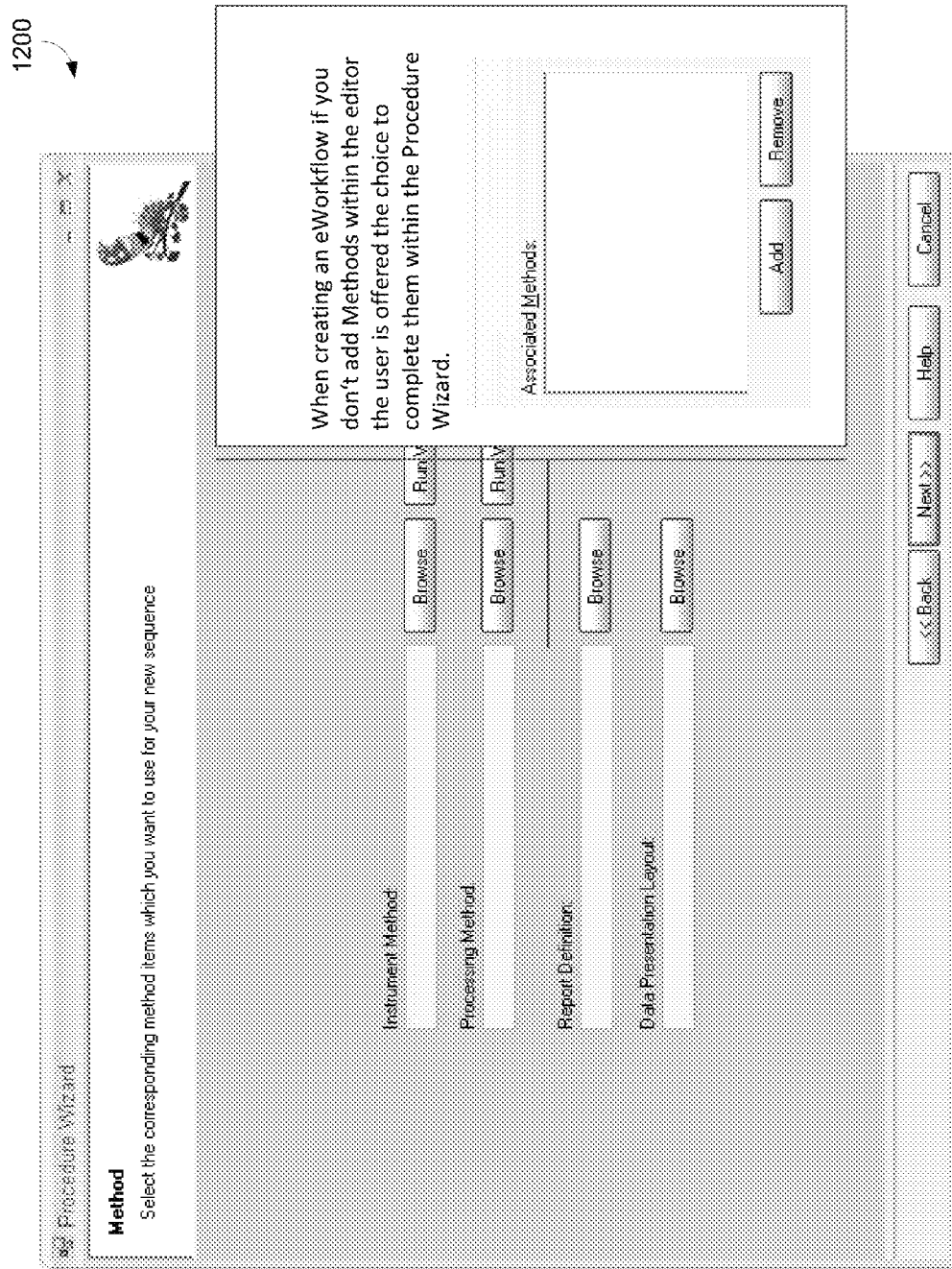
Figure 9C:
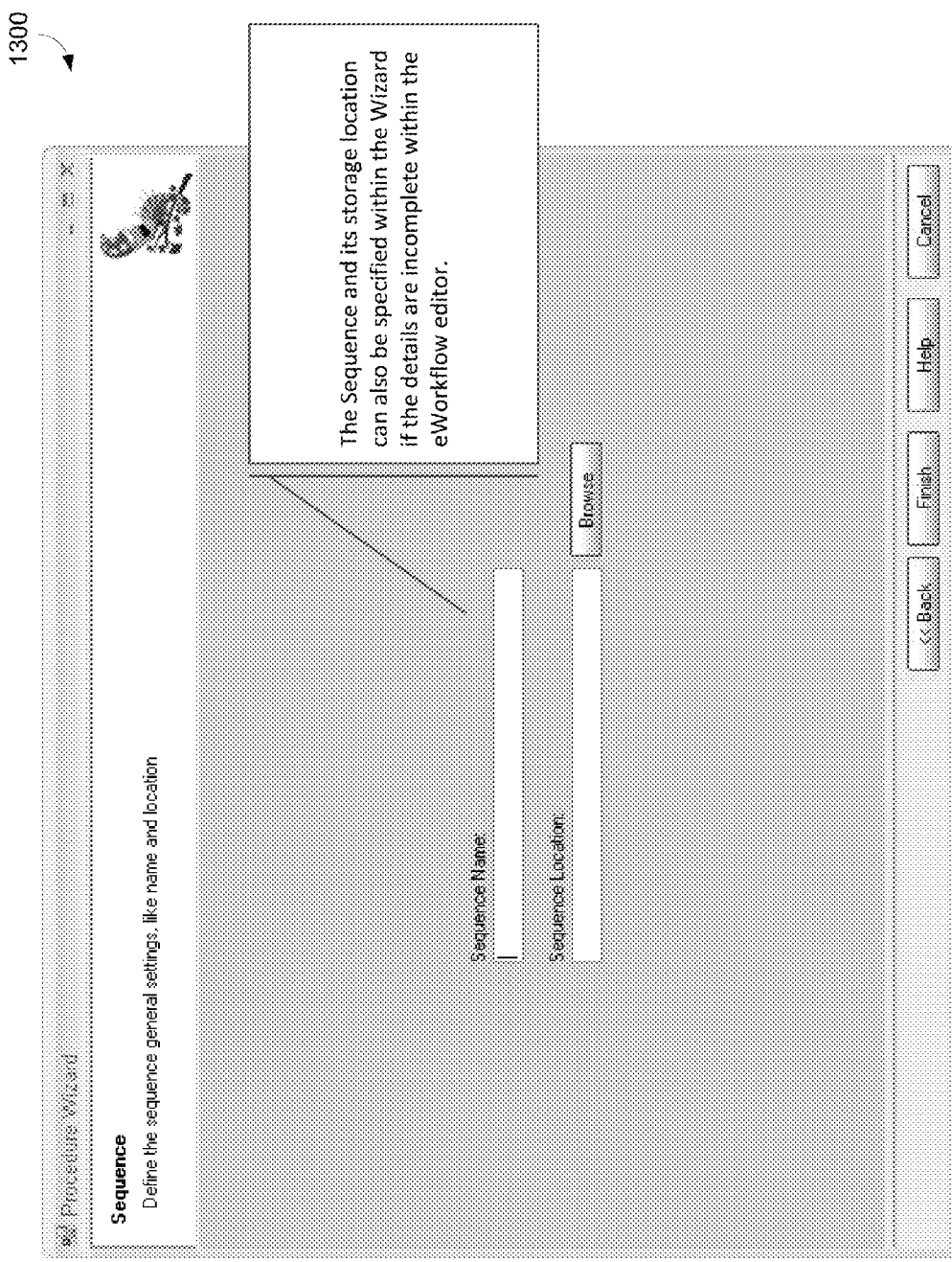

FIGS. 9A-9C illustrate how an incomplete workflow that requires additional input can be used, e.g., for a method development lab where everything but the instrument method would be defined upfront. FIG. 9A illustrates an example GUI 1100 that is the same as GUI 800 (FIG. 8A), except that the user selects a workflow titled "eWorkflow_Demonstration2," (an incomplete workflow) from pane 810. As can be seen, workflow "eWorkflow_Demonstration2" has no description 1130 and has no associated files 1160.

The workflow editor 222 provides a list 1170 of all available instruments because when the workflow "eWorkflow_Demonstration2" was created, no instruments were added by the user, for instance in section 530 (FIG. 5). The procedure wizard asks the user for missing information that is required to complete the workflow, "eWorkflow_Demonstration2." For instance, as illustrated in GUI 1200 shown in FIG. 9B, if no associated methods were added (e.g., in section 540), the procedure wizard offers the user to add an instrument method, processing method, report definition, and data presentation layout. As illustrated in the GUI 1300 shown in FIG. 9C, the sequence's general settings, such as name and storage location, an also be specified within the procedure wizard if these details were not provided earlier.

Each of the methods described herein may be governed by instructions that are stored in a computer readable storage medium and that are executed by one or more processors of one or more servers or clients. Each of the operations shown in FIG. 3 may correspond to instructions stored in a computer memory or computer readable storage medium. For instance, method 300 may be governed by instructions that are stored in a computer readable storage medium and that are executed by one or more processors (e.g., CPU(s) 202) of control device 102. Each of the operations shown in FIG. 3 may correspond to instructions stored in a computer memory or computer readable storage medium. The computer readable storage medium may include a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A computer-implemented method for implementing a sequence of analyses on an analytical laboratory instrument, comprising:
    at a computer system networked with a plurality of distinct types of analytical laboratory instruments, the computer system having one or more processors and memory storing one or more programs for execution by the one or more processors:
        receiving user inputs from a first user defining a workflow including workflow parameters for controlling a sequence of injections capable of being performed by each of the plurality of distinct types of analytical laboratory instruments, wherein the workflow parameters include sequence header information and one or more of: sample block information, bracket information and sequence footer information, in which the sequence header information defines the injections at a beginning of the sequence, in which the sample block information defines a number of injections to be performed for each physical sample, in which the bracket information defines the injections for each bracket, in which the sequence footer information defines the injections at an end of the sequence;
        receiving from a second user a request to generate the sequence of injections for execution on a user selected type of analytical instrument of the plurality of distinct types of laboratory instruments in accordance with the workflow;
        in response to the request to generate the sequence of injections, generating the executable sequence of injections according to the workflow parameters, including:
            when the user selected type is a first type of analytical lab instrument of the plurality of distinct types of analytical laboratory instruments, generating the sequence of injections by: automatically defining a first sequence header including a plurality of first header injections in accordance with the sequence header information and a first sequence of injections for the first type of analytical laboratory instrument in accordance with the one or more of the sample block, bracket and sequence footer information, including creating rules for the first sequence, wherein the rules are persistent for subsequent use of the first sequence; and
            when the user selected type is a second type of analytical lab instrument of the plurality of distinct types of analytical laboratory instruments different from the first type, generating the sequence of injections by: automatically defining a second sequence header including a plurality of second header injections in accordance with the sequence header information and a second sequence of injections for the second type of analytical laboratory instrument distinct from the first analytical laboratory instrument and in accordance with the one or more of the sample block, bracket and sequence footer information, including creating rules for the second sequence, wherein the rules are persistent for subsequent use of the second sequence; and
        causing a first instrument that is one of the first and second types of analytical lab instruments to execute sequentially the injections composing the sequence of injections that is defined by the workflow according to the created rules for the sequence of injections.

2. The method of claim 1, further comprising:
    receiving user inputs including changes to the workflow parameters for defining a respective sequence; and
    automatically updating the respective sequence based on the changes to the workflow parameters and in accordance with the rules for the respective sequence.

3. The method of claim 1, wherein the workflow parameters include one or more of: a workflow type, an instrument for which the sequence is to be defined, one or more methods that make up a sequence, and one or more associated files.

4. The method of claim 1, further comprising:
    restricting use of the first sequence header and first sequence of injections to the first type of analytical laboratory instrument and restricting the second sequence header and second sequence of injections to the second type of analytical laboratory instrument.

5. The method of claim 1, further comprising:
    collecting resulting experimental data from the one or more analytical laboratory instruments.

6. The method of claim 1, further comprising:
    receiving input from an operator for an incomplete workflow; and
    updating the incomplete workflow with the received input.

7. The method of claim 6, wherein the input includes missing information selected from the group consisting of: an instrument method, instrument type, processing method, report definition, and data presentation layout.

8. The method of claim 1, wherein the injections used in the first and second sequence headers comprise one or more standard injections occurring prior to the first and second sequences of injections respectively.

9. The method of claim 8, wherein the first and second sequence headers are different due to differences in the first and second types of analytical laboratory instruments.

10. The method of claim 8, further comprising:
receiving a maximum number of samples allowed between bracketing injections value;
wherein the first and second sequences of injections are automatically defined so as to comply with the maximum number of samples value.

11. A computer-implemented method for implementing a sequence of analyses on an analytical laboratory instrument, comprising:
on a computer system having one or more processors and memory storing one or more programs for execution by the one or more processors:
receiving user inputs for defining a workflow including workflow parameters for defining a sequence of analyses for the analytical laboratory instrument, wherein the workflow parameters include sequence header information and one or more of: sample block information, bracket information and sequence footer information, in which the sequence header information defines the injections at a beginning of the sequence, in which the sample block information defines a number of injections to be performed for each physical sample, in which the bracket information defines the injections for each bracket, in which the sequence footer information defines the injections at an end of the sequence;
automatically defining the sequence of analyses for the analytical laboratory instrument in accordance with the one or more of the sample block, bracket and sequence footer information, including creating rules for the sequence, wherein the rules are persistent for subsequent use of the sequence;
receiving user inputs including changes to a lifecycle state of the workflow, wherein the lifecycle state is one of: workflow in development, workflow ready for use, workflow approved for use, and workflow retired;
automatically updating the lifecycle state based on the changes; and
permitting use of the sequence of analyses based on the lifecycle state of the workflow and user privileges, including causing the analytical laboratory instrument to execute sequentially analyses composing the sequence of analyses according to the created rules for the sequence, the updated lifecycle state of the workflow and the user privileges.

12. The method of claim 11, wherein the bracket information includes one or more of: maximum samples per bracket, maximum brackets per sequence, number of alternate brackets, and use bracket block after sequence header.

13. The method of claim 11, further comprising:
providing a plurality of user selection options for changes to the lifecycle state of the workflow, including at least two of: workflow in development, workflow ready for use, workflow approved for use, and workflow retired; and
wherein the receiving user inputs comprises receiving a user selection of one of the provided options for changes to the lifecycle state.

14. A set of graphical user interfaces to assist a user in a workflow for defining a sequence of analyses for each of at least two distinct types of analytical laboratory instruments of a plurality of distinct types of analytical laboratory instruments networked with a computer system, the graphical user interfaces presented on the computer system with memory, a display, and one or more processors to execute one or more programs stored in the memory, the graphical user interface, comprising:
a first section presented on the display for receiving user inputs defining a workflow including changes to a lifecycle state of the workflow, wherein the lifecycle state is one of: workflow in development, workflow ready for use, workflow approved for use, and workflow retired, wherein the workflow parameters include sequence header information and one or more of: sample block information, bracket information and sequence footer information, in which the sequence header information defines the injections at a beginning of the sequence, in which the sample block information defines a number of injections to be performed for each physical sample, in which the bracket information defines the injections for each bracket, in which the sequence footer information defines the injections at an end of the sequence;
a second section presented on the display for receiving user inputs including workflow parameters associated with the workflow, wherein the workflow parameters include one or more of: a workflow type, sequence header information for a first instrument for which the sequence is to be defined, one or more methods that make up the sequence, and one or more associated files, wherein in accordance with the one or more of the sample block, bracket and sequence footer information, the user inputs control a first sequence header and a second sequence header and also control a first sequence and a second sequence of injections performed respectively by a first type and a second type of at least two distinct types of analytical laboratory instruments of the plurality of analytical laboratory instruments, the first sequence and the second sequence of analyses being persistent for subsequent use; and
wherein the computer system is configured to cause an analytical laboratory instrument that is one of the first and second types of analytical lab instruments to execute sequentially analyses composing one of the first and second sequences of analyses according to both the created rules for the respective sequence of analyses and the lifecycle state.

15. The graphical user interface of claim 14, including a sequence setting section presented on the display wherein the sequence setting include one or more of: report definition, data presentation layout, preferred channel, sequence name, sequence location, and sequence description.

16. The graphical user interface of claim 14, including a sequence layout parameters section presented on the display wherein the sequence layout parameters include one or more of: maximum samples per bracket, maximum brackets per sequence, number of alternating brackets, number of sequence headers, use of bracket block after the sequence header, sample block information, and sequence footer information.

17. The graphical user interface of claim 14, including an option allowing a user to restrict use of the first sequence header and first sequence of injections to the first type of analytical laboratory instrument and restricting the second sequence header and second sequence of injections to the second type of analytical laboratory instrument.

18. A non-transitory computer readable storage medium storing one or more programs configured for execution by a server computer networked with a plurality of distinct types of analytical laboratory instruments, the one or more programs comprising instructions for:
receiving user inputs from a first user defining a workflow including workflow parameters for controlling a sequence of injections capable of being performed by each of the plurality of distinct types of analytical laboratory instruments, wherein the workflow parameters include sequence header information and one or more of: sample block information, bracket information and sequence footer information, in which the sequence header information defines the injections at a beginning of the sequence, in which the sample block information defines a number of injections to be performed for each physical sample, in which the bracket information defines the injections for each bracket, in which the sequence footer information defines the injections at an end of the sequence;
receiving from a second user a request to generate the sequence of injections for execution on a user selected type of analytical instrument of the plurality of distinct types of laboratory instruments in accordance with the workflow;
in response to the request to generate the sequence of injections, generating the executable sequence of injections according to the workflow parameters, including:
when the user selected type is a first type of analytical lab instrument of the plurality of distinct types of analytical laboratory instruments, generating the sequence of injections by: automatically defining a first sequence header including a plurality of first header injections in accordance with the sequence header information and a first sequence of injections for the first type of analytical laboratory instrument in accordance with the one or more of the sample block, bracket and sequence footer information, including creating rules for the first sequence, wherein the rules are persistent for subsequent use of the first sequence; and
when the user selected type is a second type of analytical lab instrument of the plurality of distinct types of analytical laboratory instruments different from the first type, generating the sequence of injections by: automatically defining a second sequence header including a plurality of second header injections in accordance with the sequence header information and a second sequence of injections for the second type of analytical laboratory instrument distinct from the first analytical laboratory instrument and in accordance with the one or more of the sample block, bracket and sequence footer information, including creating rules for the second sequence, wherein the rules are persistent for subsequent use of the second sequence; and
causing a first instrument that is one of the first and second types of analytical lab instruments to execute sequentially the injections composing the sequence of injections that is defined by the workflow according to the created rules for the sequence of injections.

19. The computer readable storage medium of claim 18, further comprising instructions for:
receiving user inputs including changes to the workflow parameters for defining a respective sequence; and
automatically updating the respective sequence based on the changes to the workflow parameters and in accordance with the rules for the respective sequence.

20. The computer readable storage medium of claim 18, wherein the workflow parameters include one or more of: a workflow type, an instrument for which the sequence is to be defined, one or more methods that make up a sequence, and one or more associated files.

21. The computer readable storage medium of claim 18, further comprising instructions for:
restricting use of the first sequence header and first sequence of injections to the first type of analytical laboratory instrument and restricting the second sequence header and second sequence of injections to the second type of analytical laboratory instrument.

22. The computer readable storage medium of claim 18, further comprising instructions for:
receiving user inputs including changes to a lifecycle state of the workflow, wherein the lifecycle state is one of: workflow in development, workflow ready for use, workflow approved for use, and workflow retired;
automatically updating the lifecycle state of the workflow based on the changes; and permitting use of the sequence based on the lifecycle state of the workflow and user privileges.

23. The computer readable storage medium of claim 18, further comprising instructions for:
enabling a user to provide sequence layout parameters, including one or more of: maximum samples per bracket, maximum brackets per sequence, number of alternating brackets, number of sequence headers, use of bracket block after the sequence header, sample block information, and sequence footer information.

24. The computer readable storage medium of claim 18, further comprising instructions for:
collecting resulting experimental data from the one or more analytical laboratory instruments.

25. The computer readable storage medium of claim 18, further comprising instructions for:
receiving input from an operator for an incomplete workflow; and
updating the incomplete workflow with the received input.

26. A computer system, comprising:
a plurality distinct types of networked laboratory instruments one or more processors;
memory; and
one or more programs stored in the memory, the one or more programs comprising instructions for:
receiving user inputs from a first user defining a workflow including workflow parameters for controlling a sequence of injections capable of being performed by each of the plurality of distinct types of analytical laboratory instruments, wherein the workflow parameters include sequence header information and one or more of: sample block information, bracket information and sequence footer information, in which the sequence header information defines the injections at a beginning of the sequence, in which the sample block information defines a number of injections to be performed for each physical sample, in which the bracket information defines the injections for each bracket, in which the sequence footer information defines the injections at an end of the sequence;
receiving from a second user a request to generate the sequence of injections for execution on a user selected type of analytical instrument of the plurality of distinct types of laboratory instruments in accordance with the workflow;

in response to the request to generate the sequence of injections, generating the executable sequence of injections according to the workflow parameters, including:

when the user selected type is a first type of analytical lab instrument of the plurality of distinct types of analytical laboratory instruments, generating the sequence of injections by: automatically defining a first sequence header including a plurality of first header injections in accordance with the sequence header information and a first sequence of injections for the first type of analytical laboratory instrument in accordance with the one or more of the sample block, bracket and sequence footer information, including creating rules for the first sequence, wherein the rules are persistent for subsequent use of the first sequence; and when the user selected type is a second type of analytical lab instrument of the plurality of distinct types of analytical laboratory instruments different from the first type, generating the sequence of injections by: automatically defining a second sequence header including a plurality of second header injections in accordance with the sequence header information and a second sequence of injections for the second type of analytical laboratory instrument distinct from the first analytical laboratory instrument and in accordance with the one or more of the sample block, bracket and sequence footer information, including creating rules for the second sequence, wherein the rules are persistent for subsequent use of the second sequence; and causing a first instrument that is one of the first and second types of analytical lab instruments to execute sequentially the injections composing the sequence of injections that is defined by the workflow according to the created rules for the sequence of injections.

27. The system of claim 26, further comprising instructions for:

receiving user inputs including changes to the workflow parameters for defining a respective sequence; and automatically updating the respective sequence based on the changes to the workflow parameters and in accordance with the rules for the respective sequence.

28. The system of claim 26, wherein the workflow parameters include one or more of: a workflow type, an instrument for which the sequence is to be defined, one or more methods that make up a sequence, and one or more associated files.

29. The system of claim 26, further comprising instructions for:

restricting use of the first sequence header and first sequence of injections to the first type of analytical laboratory instrument and restricting the second sequence header and second sequence of injections to the second type of analytical laboratory instrument.

30. The system of claim 26, further comprising instructions for:

receiving user inputs including changes to a lifecycle state of the workflow, wherein the lifecycle state is one of: workflow in development, workflow ready for use, workflow approved for use, and workflow retired;

automatically updating the lifecycle state of the workflow based on the changes; and permitting use of the sequence based on the lifecycle state of the workflow and user privileges.

31. The system of claim 26, further comprising instructions for:

enabling a user to provide sequence layout parameters, including one or more of: maximum samples per bracket, maximum brackets per sequence, number of alternating brackets, number of sequence headers, use of bracket block after the sequence header, sample block information, and sequence footer information.

32. The system of claim 26, further comprising instructions for:

collecting resulting experimental data from the one or more analytical laboratory instruments.

33. The system of claim 26, further comprising instructions for:

receiving input from an operator for an incomplete workflow; and updating the incomplete workflow with the received input.

34. The system of claim 26, wherein the plurality of distinct types of analytical laboratory instruments are selected from the group comprising:

chromatography instruments, optical spectrometers, nuclear magnetic resonance spectroscopy (NMR) spectrometers, mass spectrometers, radioactivity detectors, refractive index detectors, light scattering detectors, and ultraviolet-visible spectroscopy (UV/Vis) detectors.

35. The system of claim 26, wherein the plurality of distinct types of analytical laboratory instruments are selected from the group comprising a plurality of distinct types of chromatography instruments.

* * * * *